(12) United States Patent
Shalev

(10) Patent No.: US 7,908,000 B2
(45) Date of Patent: *Mar. 15, 2011

(54) TRANSMUCOSAL ELECTRICAL STIMULATION

(75) Inventor: Alon Shalev, Ra'anana (IL)

(73) Assignee: Brainsgate Ltd., Caesarea (IL)

( * ) Notice: Subject to any disclaimer, the term of this patent is extended or adjusted under 35 U.S.C. 154(b) by 598 days.

This patent is subject to a terminal disclaimer.

(21) Appl. No.: 11/931,154

(22) Filed: Oct. 31, 2007

(65) Prior Publication Data

US 2008/0172102 A1    Jul. 17, 2008

Related U.S. Application Data

(60) Division of application No. 11/349,020, filed on Feb. 7, 2006, now Pat. No. 7,561,919, which is a continuation-in-part of application No. 10/783,113, filed on Feb. 20, 2004, now Pat. No. 7,117,033.

(51) Int. Cl.
*A61N 1/00* (2006.01)

(52) U.S. Cl. .......................................................... 607/2

(58) Field of Classification Search ................ 607/2, 45, 607/46
See application file for complete search history.

(56) References Cited

U.S. PATENT DOCUMENTS

| | | | |
|---|---|---|---|
| 4,867,164 A | 9/1989 | Zabara | |
| 4,907,602 A | 3/1990 | Sanders | |
| 4,979,511 A | 12/1990 | Terry, Jr. | |
| 5,154,172 A | 10/1992 | Terry, Jr. et al. | |
| 5,179,950 A | 1/1993 | Stanislaw | |
| 5,186,170 A | 2/1993 | Varrichio et al. | |
| 5,188,104 A | 2/1993 | Wernicke et al. | |
| 5,205,285 A | 4/1993 | Baker, Jr. | |
| 5,215,086 A | 6/1993 | Terry, Jr. et al. | |
| 5,215,089 A | 6/1993 | Baker, Jr. | |
| 5,222,494 A | 6/1993 | Baker, Jr. | |
| 5,223,254 A | 6/1993 | Paradiso et al. | |
| 5,231,988 A | 8/1993 | Wernicke et al. | |
| 5,235,980 A | 8/1993 | Varrichio et al. | |
| 5,237,991 A | 8/1993 | Baker, Jr. et al. | |
| 5,251,634 A | 10/1993 | Weinberg | |
| 5,263,480 A | 11/1993 | Wernicke et al. | |
| 5,269,303 A | 12/1993 | Wernicke et al. | |
| 5,299,569 A | 4/1994 | Wernicke et al. | |
| 5,304,206 A | 4/1994 | Baker, Jr. et al. | |

(Continued)

FOREIGN PATENT DOCUMENTS

CA    2 408 097    11/2001

(Continued)

OTHER PUBLICATIONS

Supplementary European Search Report dated Oct. 27, 2009 which issued during the prosecution of applicant's European Patent Application No. 04 77 0568.

(Continued)

*Primary Examiner* — Scott M Getzow
(74) *Attorney, Agent, or Firm* — RatnerPrestia

(57) ABSTRACT

Apparatus is provided for modifying a property of a brain of a subject, including at least one electrode, configured to be positioned in a vicinity of a mucous membrane of a palate of an oral cavity of the subject. A control unit is configured to drive the electrode to apply an electrical current to the mucous membrane, and to configure the current to be capable of inducing an increase in cerebral blood flow (CBF) of the subject. Other embodiments are also described.

13 Claims, 13 Drawing Sheets

U.S. PATENT DOCUMENTS

| | | |
|---|---|---|
| 5,304,632 A | 4/1994 | Vaudry et al. |
| 5,314,495 A | 5/1994 | Kovacs |
| 5,330,515 A | 7/1994 | Rutecki et al. |
| 5,335,657 A | 8/1994 | Terry, Jr. et al. |
| 5,351,394 A | 10/1994 | Weinberg |
| 5,531,778 A | 7/1996 | Maschino et al. |
| 5,540,730 A | 7/1996 | Terry, Jr. et al. |
| 5,571,150 A | 11/1996 | Wernicke et al. |
| 5,639,853 A | 6/1997 | Paradiso et al. |
| 5,707,400 A | 1/1998 | Terry, Jr. et al. |
| 5,716,377 A | 2/1998 | Rise et al. |
| 5,725,471 A | 3/1998 | Davey et al. |
| 5,752,515 A | 5/1998 | Jolesz et al. |
| 5,756,071 A | 5/1998 | Mattern et al. |
| 5,792,067 A | 8/1998 | Karell |
| 5,928,272 A | 7/1999 | Adkins et al. |
| 5,938,689 A | 8/1999 | Fischell et al. |
| 5,978,702 A | 11/1999 | Ward et al. |
| 6,006,124 A | 12/1999 | Fischell et al. |
| 6,016,449 A | 1/2000 | Fischell et al. |
| 6,061,593 A | 5/2000 | Fischell et al. |
| 6,066,163 A | 5/2000 | John |
| 6,086,525 A | 7/2000 | Davey et al. |
| 6,128,538 A | 10/2000 | Fischell et al. |
| 6,134,474 A | 10/2000 | Fischell et al. |
| 6,161,045 A | 12/2000 | Fischell et al. |
| 6,205,359 B1 | 3/2001 | Boveja |
| 6,230,049 B1 | 5/2001 | Fischell et al. |
| 6,232,326 B1 | 5/2001 | Nelson |
| 6,277,841 B1 | 8/2001 | Rajagopalan et al. |
| 6,325,475 B1 | 12/2001 | Hayes et al. |
| 6,338,715 B1 | 1/2002 | Hayes et al. |
| 6,341,236 B1 | 1/2002 | Osorio et al. |
| 6,343,226 B1 | 1/2002 | Sunde et al. |
| 6,353,754 B1 | 3/2002 | Fischell et al. |
| 6,354,299 B1 | 3/2002 | Fischell et al. |
| 6,360,122 B1 | 3/2002 | Fischell et al. |
| 6,405,079 B1 | 6/2002 | Ansarinia |
| 6,415,184 B1 | 7/2002 | Ishikawa et al. |
| 6,427,086 B1 | 7/2002 | Fischell et al. |
| 6,432,986 B2 | 8/2002 | Levin |
| 6,459,936 B2 | 10/2002 | Fischell et al. |
| 6,466,822 B1 | 10/2002 | Pless |
| 6,470,212 B1 | 10/2002 | Weijand et al. |
| 6,473,639 B1 | 10/2002 | Fischell et al. |
| 6,473,644 B1 | 10/2002 | Terry, Jr. et al. |
| 6,480,743 B1 | 11/2002 | Kirkpatrick et al. |
| 6,491,940 B1 | 12/2002 | Levin |
| 6,526,318 B1 | 2/2003 | Ansarinia |
| 6,529,774 B1 | 3/2003 | Greene |
| 6,531,454 B1 | 3/2003 | Leary et al. |
| 6,587,719 B1 | 7/2003 | Barrett et al. |
| 6,591,137 B1 | 7/2003 | Fischell et al. |
| 6,591,138 B1 | 7/2003 | Fischell et al. |
| 6,597,953 B2 | 7/2003 | Boling |
| 6,597,954 B1 | 7/2003 | Pless et al. |
| 6,606,521 B2 | 8/2003 | Paspa et al. |
| 6,609,025 B2 | 8/2003 | Barrett et al. |
| 6,609,956 B2 | 8/2003 | Margaria |
| 6,618,623 B1 | 9/2003 | Pless et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,640,137 B2 | 10/2003 | MacDonald |
| 6,647,296 B2 | 11/2003 | Fischell et al. |
| 6,662,035 B2 | 12/2003 | Sochor |
| 6,671,555 B2 | 12/2003 | Gielen et al. |
| 6,671,556 B2 | 12/2003 | Osorio et al. |
| 6,690,974 B2 | 2/2004 | Archer et al. |
| 6,735,474 B1 | 5/2004 | Loeb et al. |
| 6,735,475 B1 | 5/2004 | Whitehurst et al. |
| 6,788,975 B1 | 9/2004 | Whitehurst et al. |
| 6,793,664 B2 | 9/2004 | Mazzocchi et al. |
| 6,810,285 B2 | 10/2004 | Pless et al. |
| 6,811,788 B2 | 11/2004 | Yu |
| 6,853,858 B2 | 2/2005 | Shalev |
| 6,905,827 B2 | 6/2005 | Wohlgemuth et al. |
| 6,922,590 B1 | 7/2005 | Whitehurst |
| 2001/0004644 A1 | 6/2001 | Levin |
| 2002/0026652 A1 | 2/2002 | Allen et al. |
| 2002/0044919 A1 | 4/2002 | Yu |
| 2002/0099412 A1 | 7/2002 | Fischell et al. |
| 2002/0099417 A1 | 7/2002 | Naritoku |
| 2002/0133841 A1 | 9/2002 | Leviten |
| 2002/0169307 A1 | 11/2002 | Klein |
| 2002/0169485 A1 | 11/2002 | Pless et al. |
| 2003/0005473 A1 | 1/2003 | Brennan et al. |
| 2003/0005477 A1 | 1/2003 | Leviten |
| 2003/0013136 A1 | 1/2003 | Balser et al. |
| 2003/0014772 A1 | 1/2003 | Allen |
| 2003/0018988 A1 | 1/2003 | Allen et al. |
| 2003/0018989 A1 | 1/2003 | Brennan et al. |
| 2003/0036781 A1 | 2/2003 | Nuttin et al. |
| 2003/0050527 A1 | 3/2003 | Fox et al. |
| 2003/0051268 A1 | 3/2003 | Allen |
| 2003/0056238 A1 | 3/2003 | Wisotzkey |
| 2003/0073917 A1 | 4/2003 | Echauz et al. |
| 2003/0074033 A1 | 4/2003 | Pless et al. |
| 2003/0079742 A1 | 5/2003 | Giroux |
| 2003/0106083 A1 | 6/2003 | Allen |
| 2003/0131367 A1 | 7/2003 | Guenther et al. |
| 2003/0133877 A1 | 7/2003 | Levin |
| 2003/0144711 A1 | 7/2003 | Pless et al. |
| 2003/0149457 A1 | 8/2003 | Tcheng et al. |
| 2003/0166099 A1 | 9/2003 | Sabbadini et al. |
| 2003/0166279 A1 | 9/2003 | Sabbadini et al. |
| 2003/0172390 A1 | 9/2003 | Wisotzkey et al. |
| 2003/0176892 A1 | 9/2003 | Shalev |
| 2003/0176898 A1 | 9/2003 | Gross et al. |
| 2003/0177514 A1 | 9/2003 | Leviten |
| 2003/0190601 A1 | 10/2003 | Sabbadini et al. |
| 2003/0190683 A1 | 10/2003 | Sabbadini et al. |
| 2003/0190749 A1 | 10/2003 | Surber et al. |
| 2003/0194714 A1 | 10/2003 | Sabbadini et al. |
| 2003/0195588 A1 | 10/2003 | Fischell et al. |
| 2003/0195602 A1 | 10/2003 | Boling |
| 2003/0198995 A1 | 10/2003 | Sabbadini et al. |
| 2003/0198996 A1 | 10/2003 | Surber et al. |
| 2003/0199005 A1 | 10/2003 | Sabbadini et al. |
| 2003/0199088 A1 | 10/2003 | Sabbadini et al. |
| 2003/0199089 A1 | 10/2003 | Surber et al. |
| 2003/0202937 A1 | 10/2003 | Sabbadini et al. |
| 2003/0203411 A1 | 10/2003 | Sabbadini et al. |
| 2003/0203481 A1 | 10/2003 | Surber et al. |
| 2003/0207833 A1 | 11/2003 | Berkley et al. |
| 2003/0211086 A1 | 11/2003 | Berkley et al. |
| 2003/0211599 A1 | 11/2003 | Sabbadini et al. |
| 2003/0219408 A1 | 11/2003 | Sabbadini et al. |
| 2003/0219888 A1 | 11/2003 | Segall et al. |
| 2003/0224369 A1 | 12/2003 | Surber et al. |
| 2003/0224444 A1 | 12/2003 | Sabbadini et al. |
| 2003/0232335 A1 | 12/2003 | Surber et al. |
| 2004/0015068 A1 | 1/2004 | Shalev et al. |
| 2004/0033491 A1 | 2/2004 | Alsobrook, II et al. |
| 2004/0054297 A1 | 3/2004 | Wingeier et al. |
| 2004/0133248 A1 | 7/2004 | Frei et al. |
| 2004/0136950 A1 | 7/2004 | Ni et al. |
| 2004/0136951 A1 | 7/2004 | Ni et al. |
| 2004/0153129 A1 | 8/2004 | Pless et al. |
| 2004/0210269 A1 | 10/2004 | Shalev et al. |
| 2004/0220644 A1 | 11/2004 | Shalev et al. |
| 2005/0020519 A1 | 1/2005 | Albiston et al. |
| 2005/0065427 A1 | 3/2005 | Magill et al. |
| 2005/0074506 A1 | 4/2005 | Natan et al. |
| 2005/0112090 A9 | 5/2005 | Ni et al. |
| 2005/0113877 A1 | 5/2005 | Spinelli et al. |
| 2005/0118187 A1 | 6/2005 | Yu |
| 2005/0137646 A1 | 6/2005 | Wallace et al. |
| 2005/0137647 A1 | 6/2005 | Wallace et al. |
| 2005/0154419 A1 | 7/2005 | Whitehurst et al. |
| 2005/0159790 A1 | 7/2005 | Shalev |
| 2005/0266099 A1 | 12/2005 | Shalev |
| 2007/0083245 A1 | 4/2007 | Lamensdorf et al. |

FOREIGN PATENT DOCUMENTS

| | | |
|---|---|---|
| CA | 2 401 098 A1 | 1/2002 |
| CA | 2 433 376 A1 | 8/2002 |

| | | |
|---|---|---|
| EP | 0 814 089 A2 | 12/1997 |
| EP | 0 610 301 B1 | 2/1998 |
| EP | 0 726 791 B1 | 6/2000 |
| EP | 0 588 957 B1 | 9/2000 |
| EP | 0 613 389 B1 | 9/2001 |
| EP | 1 559 369 A1 | 8/2005 |
| WO | WO 89/02935 | 4/1989 |
| WO | WO 93/03762 | 3/1993 |
| WO | WO 93/09841 | 5/1993 |
| WO | WO 93/25271 | 12/1993 |
| WO | WO 94/00185 | 1/1994 |
| WO | WO 94/00188 | 1/1994 |
| WO | WO 94/00189 | 1/1994 |
| WO | WO 95/14028 | 5/1995 |
| WO | WO 98/30709 | 7/1998 |
| WO | WO 99/03473 | 1/1999 |
| WO | WO 99/56822 | 11/1999 |
| WO | WO 00/44432 | 8/2000 |
| WO | WO 01/26729 A1 | 4/2001 |
| WO | WO 01/38581 A2 | 5/2001 |
| WO | WO 01/43733 A2 | 6/2001 |
| WO | WO 01/43733 A3 | 6/2001 |
| WO | WO 01/52868 A1 | 7/2001 |
| WO | WO 01/53455 A2 | 7/2001 |
| WO | WO 01/57190 A2 | 8/2001 |
| WO | WO 01/64835 A2 | 9/2001 |
| WO | WO 01/67855 A2 | 9/2001 |
| WO | WO 01/85094 A2 | 11/2001 |
| WO | WO 01/85094 A3 | 11/2001 |
| WO | WO 01/88088 A2 | 11/2001 |
| WO | WO 01/97905 A1 | 12/2001 |
| WO | WO 01/97906 A2 | 12/2001 |
| WO | WO 01/98508 A2 | 12/2001 |
| WO | WO 02/04068 A1 | 1/2002 |
| WO | WO 02/06339 A2 | 1/2002 |
| WO | WO 02/06445 A2 | 1/2002 |
| WO | WO 02/16439 A2 | 2/2002 |
| WO | WO 02/32504 A2 | 4/2002 |
| WO | WO 02/32504 A3 | 4/2002 |
| WO | WO 02/42735 A2 | 5/2002 |
| WO | WO 02/45498 A2 | 6/2002 |
| WO | WO 02/46229 A2 | 6/2002 |
| WO | WO 02/46390 A2 | 6/2002 |
| WO | WO 02/46409 A2 | 6/2002 |
| WO | WO 02/47477 A2 | 6/2002 |
| WO | WO 02/48345 A2 | 6/2002 |
| WO | WO 02/057450 A2 | 7/2002 |
| WO | WO 02/059315 A2 | 8/2002 |
| WO | WO 02/062291 A2 | 8/2002 |
| WO | WO 02/064791 A2 | 8/2002 |
| WO | WO 02/066643 A2 | 8/2002 |
| WO | WO 02/068029 A2 | 9/2002 |
| WO | WO 02/068029 A3 | 9/2002 |
| WO | WO 02/068031 A2 | 9/2002 |
| WO | WO 02/068031 A3 | 9/2002 |
| WO | WO 02/079424 A2 | 10/2002 |
| WO | WO 02/079438 A2 | 10/2002 |
| WO | WO 02/079439 A2 | 10/2002 |
| WO | WO 02/079440 A2 | 10/2002 |
| WO | WO 02/079444 A2 | 10/2002 |
| WO | WO 02/081510 A2 | 10/2002 |
| WO | WO 02/081658 A2 | 10/2002 |
| WO | WO 03/000046 A1 | 1/2003 |
| WO | WO 03/000310 A2 | 1/2003 |
| WO | WO 03/001883 A2 | 1/2003 |
| WO | WO 03/011304 A1 | 2/2003 |
| WO | WO 03/011392 A2 | 2/2003 |
| WO | WO 03/011393 A1 | 2/2003 |
| WO | WO 03/018107 A2 | 3/2003 |
| WO | WO 03/018108 A2 | 3/2003 |
| WO | WO 03/020350 A1 | 3/2003 |
| WO | WO 03/026395 A2 | 4/2003 |
| WO | WO 03/026401 A2 | 4/2003 |
| WO | WO 03/033672 A2 | 4/2003 |
| WO | WO 03/063959 A1 | 8/2003 |
| WO | WO 03/072014 A2 | 9/2003 |
| WO | WO 03/076008 A1 | 9/2003 |
| WO | WO 03/079742 A1 | 9/2003 |
| WO | WO 03/080795 A2 | 10/2003 |
| WO | WO 03/084591 A1 | 10/2003 |
| WO | WO 03/090599 A2 | 11/2003 |
| WO | WO 03/105658 A2 | 12/2003 |
| WO | WO 2004/010923 A2 | 2/2004 |
| WO | WO 2004/043217 A2 | 5/2004 |
| WO | WO 2004/043218 A2 | 5/2004 |
| WO | WO 2004/043334 A2 | 5/2004 |
| WO | WO 2004/044947 A2 | 5/2004 |
| WO | WO 2004/045242 A2 | 5/2004 |
| WO | WO 2004/064918 A1 | 8/2004 |
| WO | WO 2004/098515 A2 | 11/2004 |
| WO | WO 2004/113391 A2 | 12/2004 |
| WO | WO 2005/002467 A2 | 1/2005 |
| WO | WO 2005/015404 A2 | 2/2005 |
| WO | WO 2005/030025 A2 | 4/2005 |
| WO | WO 2005/030118 A2 | 4/2005 |
| WO | WO 2005/062829 A2 | 7/2005 |

OTHER PUBLICATIONS

Delépine, L. et al., "Plasma Protein Extravasation Induced in the Rat Dura Mater by Stimulation of the Parasympathetic Spenopalatine Ganglion," Experimental Neurology 147, 389-400, 1997, Article No. EN976614.

Hara, H. et al., "Parasympathetic Cerebrovascular Innervation: An Anterograde Tracing from the Spenopalatine Ganglion in the Rat," Neurosurgery 32(5), 822-827, May, 1993.

Kroll, R. A. et al., "Outwitting the Blood Brain Barrier for Therapeutic Purposes: Osmotic Opening and Other Means," Neurosurgery, 42(5), 1083-1099, May 1998.

Sanders, M. et al., "Efficacy of spenopalatine ganglion blockade in 66 patients suffering from cluster headache: a 12- to 70- month follow-up evaluation," Journal of Neurosurgery, 87, 876-880, Dec. 1997.

Suzuki, N. et al., "Selective Electrical Stimulation of Postganglionic Cerebrovascular Parasympathetic Nerve Fibers Originating from the Spenopalatine Ganglion Enhances Cortical Blood Flow in the Rat," Journal of Cerebral Blood Flow and Metabolism, 10:383-391, 1990.

Major, A. et al., "Odorants Presented to the Rat Nasal Cavity Increase Cortical Blood Flow," Chem. Senses, 24:665-669, 1999.

Fusco, B.M. et al., " 'Capsaicin-Sensitive' Sensory Neurons in Cluster Headache: Pathophysiological Aspects and Therapeutic Indication," Headache, 34:132-137, Mar. 1994.

Silver, W.L., "Neural and Pharmacological Basis for Nasal Irritation," in Tucker WG, Leaderer BP, Molhave L, Cain WS (eds), Sources of Indoor Air Contaminants, Annals New York Academy of Sciences, 641, 152-163, 1992.

Toda, N. et al., "Cerebral Vasodilatation Induced by Stimulation of the Pterygopalatine Ganglion and Greater Petrosal Nerve in Anesthetized Monkeys," Neuroscience 96(2): 393-398, 2000.

Roth, B.J. et al., "In vitro evaluation of a 4-leaf coil design for magnetic stimulation of peripheral nerve," Electroencephalography and Clinical Neurophysiology, 93, 68-74, 1994.

USPTO Non-Final Office Action mailed Dec. 16, 2005 for U.S. Appl. No. 10/753,882.

USPTO Non-Final Office Action mailed Oct. 4, 2005 for U.S. Appl. No. 10/294,310.

European Patent Office Search Report for Application No. EP 06 01 7239, Dec. 13, 2006.

Hotta H et al., in an article entitled, "Effects of stimulating the nucleus basalis of Meynert on blood flow and delayed neuronal death following transient ischemia in rat cerebral cortes," Jap J Phys 52:383-393 (2002).

Segher O et al., in an article entitled, "Spinal cord stimulation reducing infract volume in model of focal cerebral ischemia in rats," J Neurosurg 99(1):131-137 (2003).

Goadsby PJ et al., "Effect of stimulation of trigeminal ganglion on regional cerebral blood flow in cats," Am J Physiol 253:R270-R274, (1987).

Matsui T et al., in an article entitled, "The effects of cervical spinal cord stimulation (cSCS) on experimental stroke," Pacing Clin Electrophysiol 12(4 Pt 2):726-32 (1989).

Suzuki N et al., "Trigeminal fibre collaterals storing substance P and calcitonin gene-related peptide associate with ganglion cells containing choline acetyltransferase and vasoactive intestinal polypeptide in the sphenopalatine ganglion of the rat. An axon reflex modulating parasympathetic ganglionic activity?" Neuroscience 30:595-604 (1989).

Walters BB et al., "Cerebrovascular projections from the sphenopalatine and otic ganglia to the middle cerebral artery of the cat," Stroke 17:488-494 (1986).

Branston NM, "The physiology of the cerebrovascular parasympathetic innervation," British Journal of Neurosurgery 9:319-329 (1995).

Branston NM et al., "Contribution of cerebrovascular parasympathetic and sensory innervation to the short-term control of blood flow in rat cerebral cortex," J Cereb Blood Flow Metab 15(3):525-31 (1995).

Sun Y et al., "Neuronal nitric oxide synthase and ischemia-induced neurogenesis," J Cereb Blood Flow Metab 25(4):485-92 (2005).

Zhang F et al., "Nitric oxide donors increase blood flow and reduce brain damage in focal ischemia: evidence that nitric oxide is beneficial in the early stages of cerebral ischemia," J Cereb Blood Flow Metab 14(2):217-26 (1994).

Schmid-Elsaesser R et al., "A critical reevaluation of the intraluminal thread model of focal cerebral ischemia. Evidence of inadvertent premature reperfusion and subarachnoid hemorrhage in rats by laser-Doppler flowmetry," Stroke 29:2162-2170 (1998).

Jolliet-Riant P, Tillement JP, "Drug transfer across the blood-brain barrier and improvement of brain delivery," Fundam. Clin. Pharmacol., 13, 16-25 (1999).

Syelaz J, Hara H, Pinard E, Mraovitch S, MacKenzie ET, Edvinsson L, "Effects of stimulation of the sphenopalatine ganglion on cortical blood flow in the rat", Journal of Cerebral Blood Flow and Metabolism, 8, 875-878 (1988).

Toda N et al., "Cerebral vasodilation induced by stimulation of the pterygopalatine ganglion and greater petrosal nerve in anesthetized monkeys," Neuroscience 96(2):393-398 (2000).

Varghese et al., "Endoscopic transnasal neurolytic sphenopalatine ganglion block for head and neck cancer pain," J Laryngol Otol 115(5):385-7 (2001).

Roman GC, "Cholinergic dysfunction in vascular dementia," Curr Psychiatry Rep 7(1):18-26 (2005).

Van Gijn J et al., "Subarachnoid haemorrhage: diagnosis, causes and management," Brain 124:249-278 (2001).

Davis SM et al., "Advances in penumbra imaging with MR," Cerebrovasc Dis 17 Suppl 3:23-7 (2004).

Zausinger VS et al., "Neurological impairment in rats after transient middle cerebral artery occlusion: a comparative study under various treatment paradigms," Brain Research 863(1-2):94-105 (2000).

Phan TG et al., "Salvaging the ischaemic penumbra: more than just reperfusion?" Clin Exp Pharmacol Physiol 29(1-2):1-10 (2002).

Zhang ZG et al., "VEGF enhances angiogenesis and promotes blood-brain barrier leakage in the ischemic brain," J Clin Invest 106:829-838 (2000).

Kawamata T et al., "Intracisternal basic fibroblast growth factor (bFGF) enhances behavioral recovery following focal cerebral infarction in the rat," J Cereb Blood Flow Metab 16:542-547 (1996).

Ziche M et al., "Nitric oxide and angiogenesis," J Neurooncol 50:139-148 (2000).

Zhang R et al., "A nitric oxide donor induces neurogenesis and reduces functional deficits after stroke in rats," Ann Neurol 50:602-611 (2001).

de la Torre JC, "Vascular basis of Alzheimer's pathogenesis," Ann NY Acad Sci 977:196-215 (2002).

Hunter AJ et al., "To what extent have functional studies of ischemia in animals been useful in the assessment of potential neuroprotective agents?" Trends Pharmacol Sci 19:59-66 (1998).

Kanner AA et al., "Serum S100beta: a noninvasive marker of blood-brain barrier function and brain lesions," Cancer 97(11):2806-13 (2003).

Lee, TJF, Nitric oxide and the cerebral vascular function, J Biomed Sci 7:16-26 (2000).

Sandgren K et al., "Vasoactive intestinal peptide and nitric oxide promote survival of adult rat myenteric neurons in culture," J Neurosci Res 72(5):595-602 (2003).

Laude K et al., "NO produced by endothelial NO synthase is a mediator of delayed preconditioning-induced endothelial protection," Am J Physiol Heart Circ Physiol 284(6):H2053-60 (2003) (Epub Jan. 9, 2003).

Khan M et al., "S-Nitrosoglutathione reduces inflammation and protects brain against focal cerebral ischemia in a rat model of experimental stroke," J Cereb Blood Flow Metab 25(2):177-92 (2005).

Pluta RM, "Delayed cerebral vasospasm and nitric oxide: review, new hypothesis, and proposed treatment," Pharmacol Ther 105(1):23-56 (2005).

Reis DJ et al., "Electrical stimulation of cerebellar fastigial nucleus reduces ischemic infarction elicited by middle cerebral artery occlusion in rat," J Cereb Blood Flow Metab 11(5):810-8 (1991).

Nollet H et al., "Transcranial magnetic stimulation: review of the technique, basic principles and applications," The Veterinary Journal 166:28-42 (2003).

Devoghel JC, "Cluster headache and sphenopalatine block," Acta Anaesthesiol Belg., 32(1):101-7 (1981)—an abstract.

Delephine, et al., "Plasma Protein Extravasation Induced in the Rat Dura Mater by Stimulation of the Parasympathetic Sphenopalatine Ganglion", Experimental Neurology, 147, 389-400, 1997.

Hara et al., "Parasympathetic Cerebrovascular Innervation: An Anterograde Tracing from the Sphenopalatine Ganglion in the Rat", Neurosurgery, 32, 822-827, 1993.

G.L. Ruskell, "The Orbital Branches of the Pterygopalatine Ganglion and their Relationship with Internal Carotid Nerve Branches in Primates", J. Anat. 1970, 106, 2, pp. 323-339.

Kroll RA, Neuwelt EA, "Outwitting the Blood Brain Barrier for Therapeutic Purposes: Osmotic Opening and Other Means", Neurosurgery, 42, 1083-1100, 1998.

Sanders M, et al., "Efficacy of Sphenopalatine Ganglion Blockade in 66 Patients Suffering from Cluster Headache: A 12-70 Month Follow-Up Evaluation", Journal of Neurosurgery, 87, 876-880, 1997.

Samad TA et al., in an article entitled, "Interleukin-1beta-mediated induction of Cox-2 in the CNS contributes to inflammatory pain hypersensitivity," in Nature 410(6827):471-5 (2001).

Van de WaterBeemd, et al., "Estimation of Blood Brain Barrier Crossing of Drugs Using Molecular Size and Shape and H bonding Descriptors", Journal of Drug Targeting, 6, 151-165, 1998.

Ronald F. Young, "Electrical Stimulation of the Trigeminal nerve root for the Treatment of Chronic Facial Pain", J Neurosurg 83:72-78, 1995.

N. Suzuki, et al, "Origins and Pathways of Cerebrovascular Vasoactive Intestinal Polypeptide-Positive Nerves in Rat", J Cereb Blood Flow Metab. vol. 8 No. 5, 1988.

Zhang, R. et al., "Nitric Oxide Enhances Angiogenesis via the Synthesis of Vascular Endothelial Growth Factor and cGMP After Stroke in the Rat", Circ. Res. 2003; 92; 308-313.

USPTO Office Action dated Aug. 23, 2010 issued for U.S. Appl. No. 11/928,024.

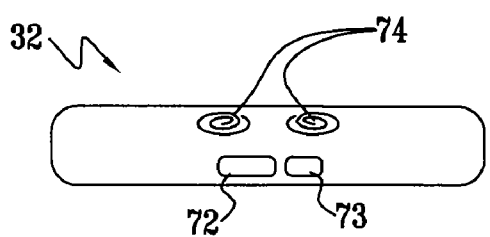
FIG. 7A
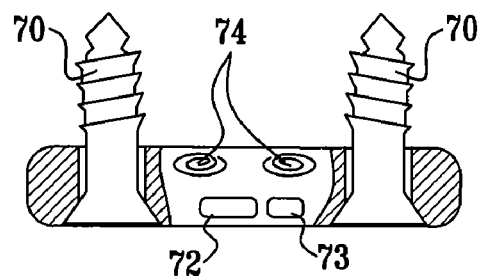
FIG. 7B
FIG. 8
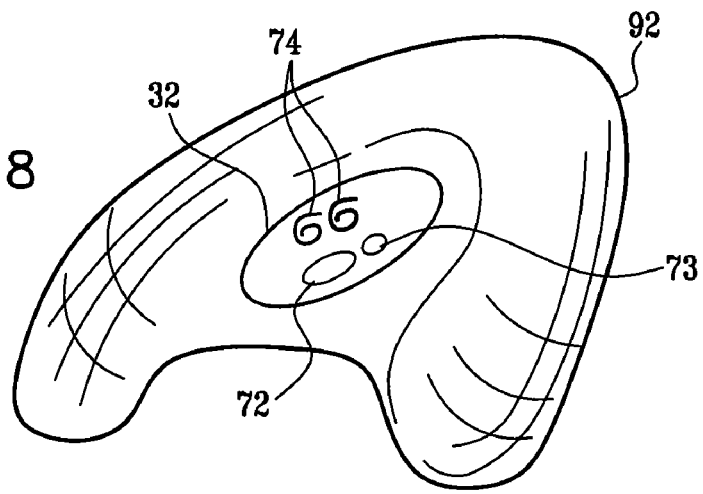
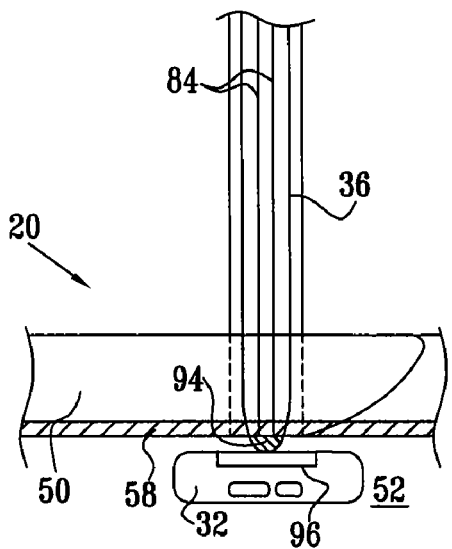
FIG. 9
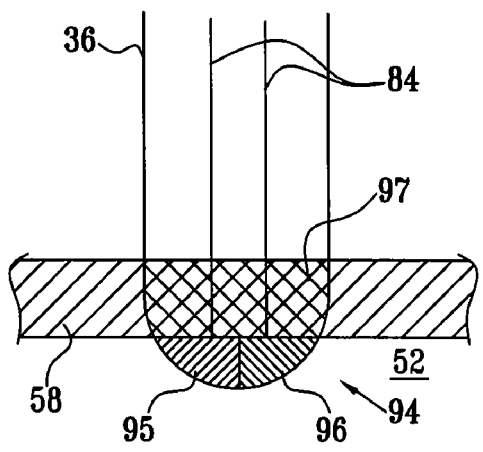
FIG. 10

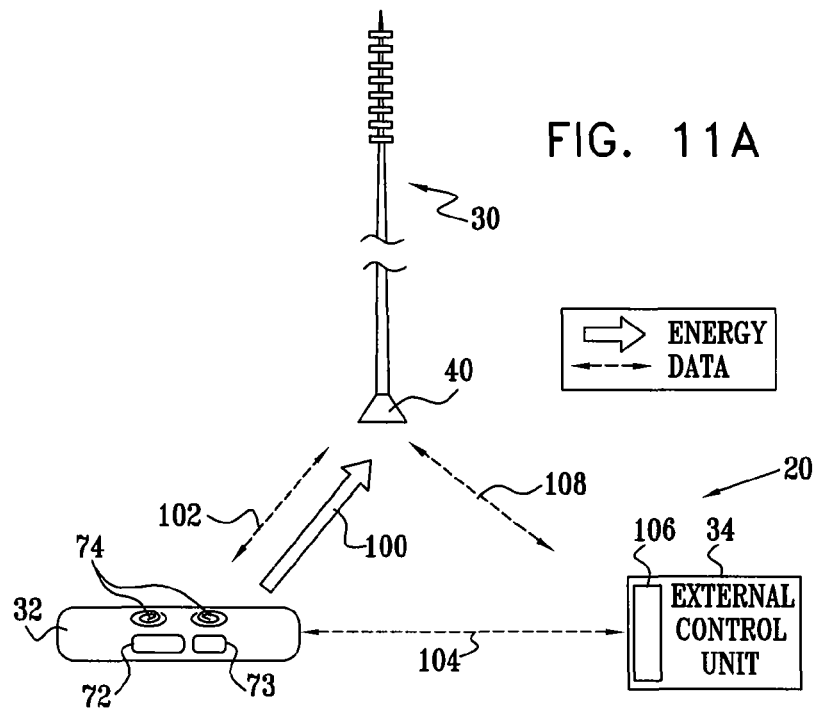
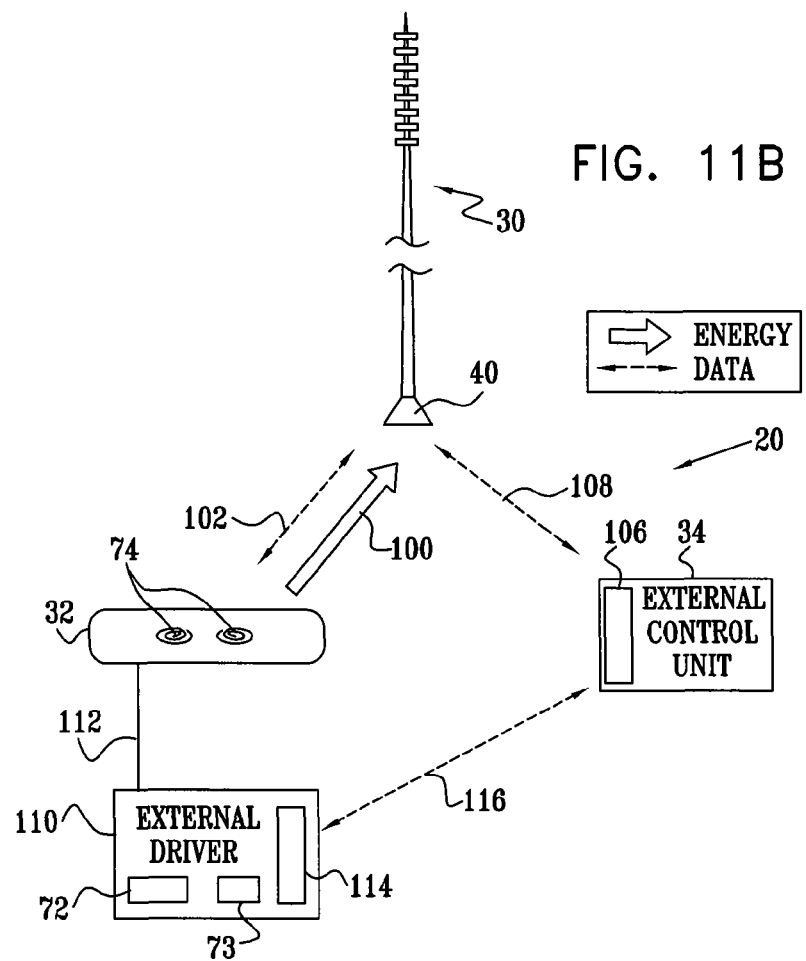

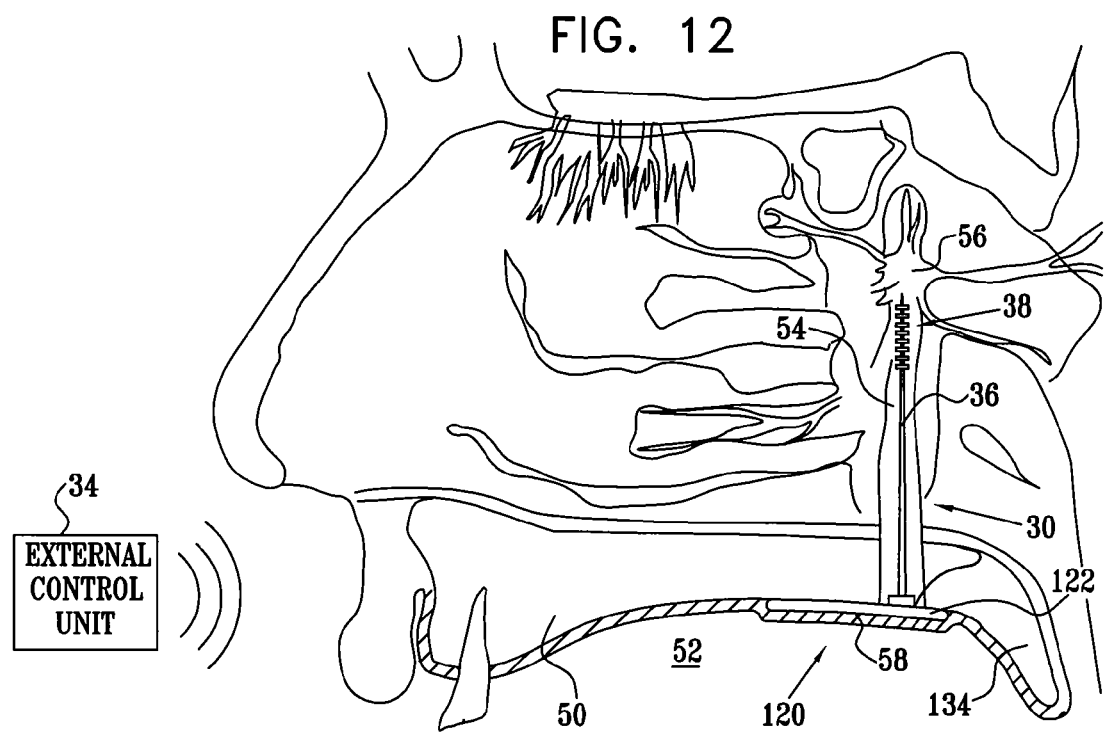

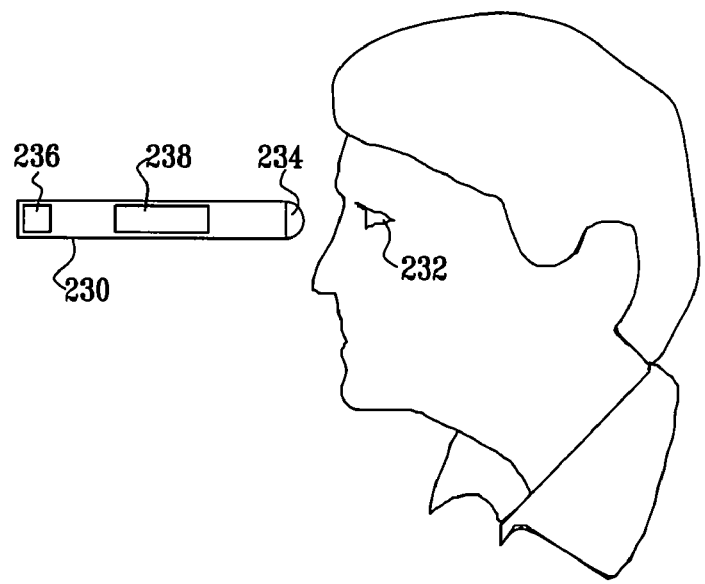
FIG. 19
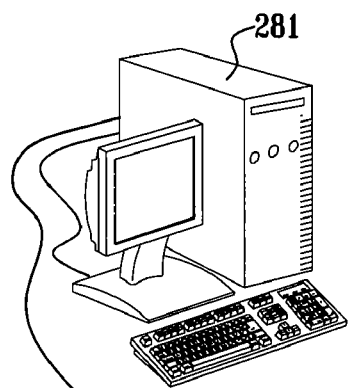
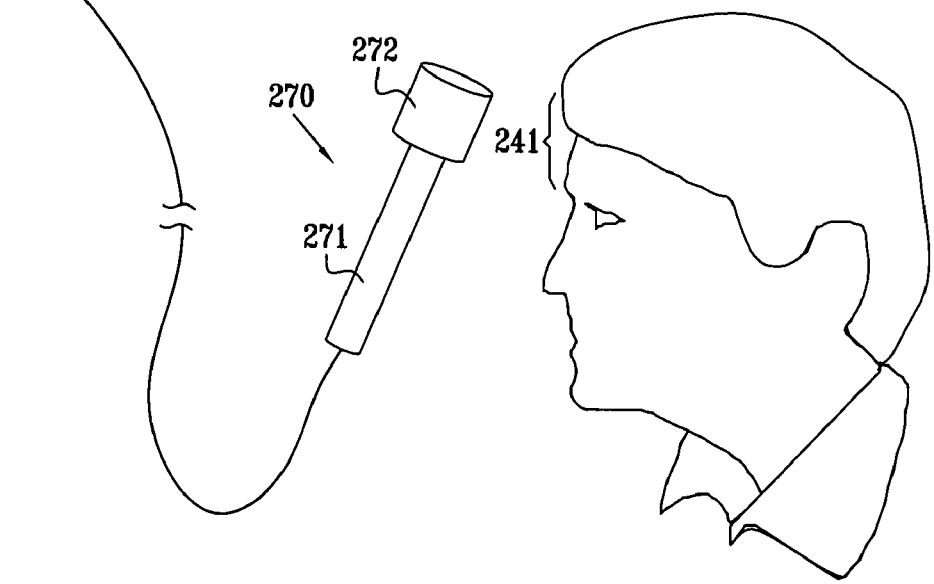
FIG. 20

FIG. 21
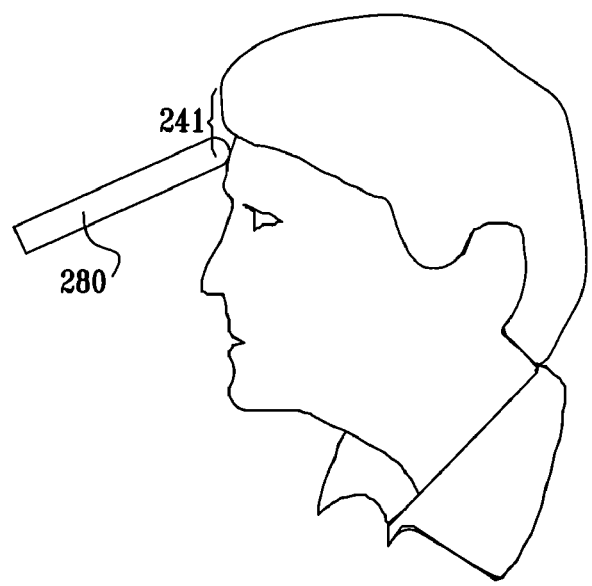
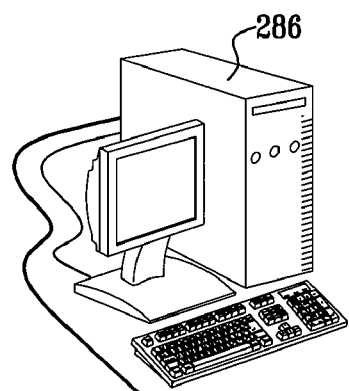
FIG. 22
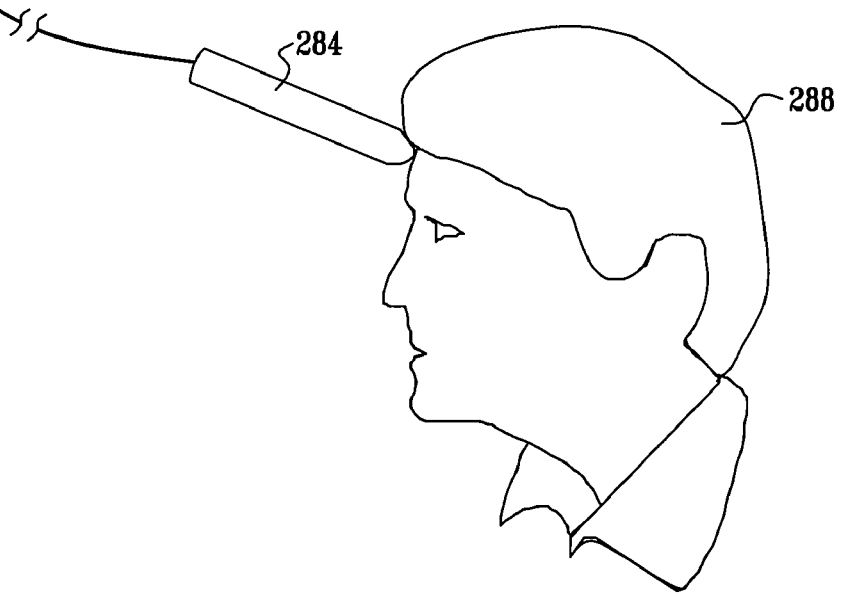

TRANSMUCOSAL ELECTRICAL STIMULATION

CROSS-REFERENCES TO RELATED APPLICATIONS

The present application is a divisional of U.S. patent application Ser. No. 11/349,020, filed Feb. 7, 2006, entitled: "SPG stimulation via the greater palatine canal, which is a continuation-in-part of U.S. patent application Ser. No. 10/783,113, filed Feb. 20, 2004, entitled, "Stimulation for acute conditions," which issued as U.S. Pat. No. 7,117,033, and is assigned to the assignee of the present application and is incorporated herein by reference.

FIELD OF THE INVENTION

The present invention relates generally to medical procedures and electrical devices. More specifically, the invention relates to the use of electrical devices for implantation in the head, for example, in the nasal cavity.

BACKGROUND OF THE INVENTION

PCT Publication WO 01/85094 to Shalev and Gross, which is assigned to the assignee of the present patent application and is incorporated herein by reference, describes apparatus for modifying a property of a brain of a patient, including electrodes applied to a sphenopalatine ganglion (SPG) or a neural tract originating in or leading to the SPG. A control unit drives the electrodes to apply a current capable of inducing (a) an increase in permeability of a blood-brain barrier (BBB) of the patient, (b) a change in cerebral blood flow of the patient, and/or (c) an inhibition of parasympathetic activity of the SPG.

U.S. Pat. No. 6,853,858 to Shalev, which is assigned to the assignee of the present application and is incorporated herein by reference, describes apparatus for delivering a Non Steroidal Anti-Inflammatory Drug (NSAID) supplied to a body of a subject for delivery to at least a portion of a central nervous system (CNS) of the subject via a systemic blood circulation of the subject. The apparatus includes a stimulator adapted to stimulate at least one site of the subject, so as to cause an increase in passage of the NSAID from the systemic blood circulation across a blood brain barrier (BBB) of the subject to the portion of the CNS, during at least a portion of the time that the NSAID is present in the blood, the site selected from the list consisting of: a sphenopalatine ganglion (SPG), an anterior ethmoidal nerve, a posterior ethmoidal nerve, a communicating branch between an anterior ethmoidal nerve and a retro-orbital branch of an SPG, a communicating branch between a posterior ethmoidal nerve and a retro-orbital branch of an SPG, a greater palatine nerve, a lesser palatine nerve, a sphenopalatine nerve, a communicating branch between a maxillary nerve and an SPG, a nasopalatine nerve, a posterior nasal nerve, an infraorbital nerve, an otic ganglion, an afferent fiber going into the otic ganglion, an efferent fiber going out of the otic ganglion, a vidian nerve, a greater superficial petrosal nerve, and a lesser deep petrosal nerve.

US Patent Application Publication 2004/0220644 to Shalev et al., which is assigned to the assignee of the present application and is incorporated herein by reference, describes a method for treating a subject, comprising positioning at least one electrode at least one site of the subject for less than about 3 hours, applying an electrical current to the site of the subject, and configuring the current to increase cerebral blood flow (CBF) of the subject, so as to treat a condition of the subject. The site is selected from the list consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve. Also described is an apparatus comprising an elongated support element having a length of between about 1.8 cm and about 4 cm, and having a proximal end and a distal end; one or more electrodes fixed to the support element in a vicinity of the distal end thereof; a receiver, fixed to the support element in a vicinity of the proximal end thereof; and a control unit, adapted to be coupled to the receiver, and adapted to drive the electrodes to apply an electrical current to tissue of the subject, and configure the current to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes.

The following patent application publications, all of which are assigned to the assignee of the present application and are incorporated herein by reference, may be of interest: WO 03/090599, WO 03/105658, WO 04/010923, WO 04/043218, WO 04/044947, WO 04/045242, WO 04/043217, WO 04/043334, WO 05/030025, and WO 05/030118.

U.S. Pat. No. 6,526,318 to Ansarinia and related PCT Publication WO 01/97905 to Ansarinia, which are incorporated herein by reference, describe a method for the suppression or prevention of various medical conditions, including pain, movement disorders, autonomic disorders, and neuropsychiatric disorders. The method includes positioning an electrode on or proximate to at least one of the patient's SPG, sphenopalatine nerves, or vidian nerves, and activating the electrode to apply an electrical signal to such nerve. In a further embodiment for treating the same conditions, the electrode used is activated to dispense a medication solution or analgesic to such nerve.

U.S. Pat. No. 6,405,079 to Ansarinia, which is incorporated herein by reference, describes a method for the suppression or prevention of various medical conditions, including pain, movement disorders, autonomic disorders, and neuropsychiatric disorders. The method includes positioning an electrode adjacent to or around a sinus, the dura adjacent a sinus, or falx cerebri, and activating the electrode to apply an electrical signal to the site. In a further embodiment for treating the same conditions, the electrode dispenses a medication solution or analgesic to the site.

U.S. Pat. No. 6,788,975 to Whitehurst et al., which is incorporated herein by reference, describes an implantable stimulator with at least two electrodes that is small enough to have the electrodes located adjacent to a nerve structure at least partially responsible for epileptic seizures. The nerve structure may include a trigeminal ganglion or ganglia, a trigeminal nerve, or a branch of a trigeminal nerve, a greater occipital nerve, lesser occipital nerve, third occipital nerve, facial nerve, glossopharyngeal nerve, or a branch of any of these neural structures. Electrical stimulation of such targets may provide significant therapeutic benefit in the management of epilepsy.

U.S. Pat. No. 5,716,377 to Rise et al., which is incorporated herein by reference, describes techniques for stimulating the brain to treat movement disorders resulting in abnormal motor behavior by means of an implantable signal generator and electrode. A sensor is used to detect the symptoms resulting from the motion disorder. A microprocessor algorithm analyzes the output from the sensor in order to regulate the stimulation delivered to the brain.

U.S. Pat. No. 6,415,184 to Ishikawa et al., which is incorporated herein by reference, describes a ball semiconductor for stimulating a mass of nervous system brain tissue for therapeutic purposes. The ball is embedded in a mass of nervous system tissue of a brain. Electrical pulses generated and transmitted to the ball by a remote electrical pulse generator system are picked up by a receiving antenna of the ball, and are applied to an electrode pair of the ball to cause the mass of nervous system tissue of the brain located between output pads of the electrode to become stimulated, as therapy for a pathological condition, such as epilepsy.

U.S. Pat. No. 6,606,521 to Paspa et al., which is incorporated herein by reference, describes an implantable medical lead having markings, which aid in the accurate localization of lead electrodes at a specific point of the brain for neurostimulation. Also described is an implantable medical lead having a removable extension that provides a minimal length of excess lead protruding from the lead insertion site. The lead and method of implantation facilitate use of a neurostimulator device that is implanted directly in a patient's cranium.

U.S. Pat. No. 6,591,138 to Fischell et al., which is incorporated herein by reference, describes a system for treating neurological conditions by low-frequency time varying electrical stimulation. The system includes an electrical device for applying such low-frequency energy, in a range below approximately 10 Hz, to the patient's brain tissue. An implantable embodiment applies direct electrical stimulation to electrodes implanted in or on the patient's brain, while a non-invasive embodiment causes a magnetic field to induce electrical currents in the patient's brain.

U.S. Pat. No. 6,343,226 to Sunde et al., which is incorporated herein by reference, describes a quadripolar deep brain stimulation electrode for treating symptoms of central and peripheral nervous system disorders, such as Parkinson's disease, epilepsy, psychiatric illness, and intractable pain. It is important to determine the optimal placement of an implanted electrode. An electrode device is described that allows stimulation of a large volume of neural tissue in combination with simultaneous microelectrode recording. The device is described as allowing for a less traumatic localization of the optimal neural stimulation area by microelectrode recording in combination with the placement of the permanent deep brain stimulation electrode.

US Patent Application Publication 2005/0065427 to Magill et al., which is incorporated herein by reference, describes a method for locating the position of a selected neural center in the central nervous system, including stimulating neurons at a first central nervous system position, measuring the field potential evoked at a second central nervous system position, and comparing the evoked field potential against a known evoked field potential from said neural center.

US Patent Application Publication 2005/0113877 to Spinelli et al., which is incorporated herein by reference, describes implantable devices and methods for treating various disorders of the pelvic floor by means of electrical stimulation of the pudendal or other nerves. Neurophysiological monitoring is utilized to assess the evoked responses of the pudendal nerve, and thereby to provide a method for determining the optimal stimulation site.

U.S. Pat. No. 5,314,495 to Kovacs, which is incorporated herein by reference, describes a microelectrode interface for localizing the stimulation and recording of action potentials at a portion of a nervous system. A circuit is described for applying current only to one or more selected pairs of microelectrodes in an array of microelectrodes. Row and column select lines, switches and multiplexes are used for passing current only between pairs of microelectrodes at selected locations in the array for stimulating a portion of a nervous system only at selected locations.

The following patents and patent publications, all of which are incorporated herein by reference, may be of interest: U.S. Pat. No. 5,756,071 to Mattern et al., U.S. Pat. No. 5,752,515 to Jolesz et al., PCT Publications WO 03/084591, WO 03/020350, WO 03/000310, WO 02/068031, and WO 02/068029 to Djupesland, US Patent Application Publication 2003/0079742 to Giroux, U.S. Pat. Nos. 5,725,471 and 6,086,525 to Davey et al., PCT Publication WO 02/32504 to Zanger et al., US Patent Application Publication 2003/0050527 to Fox et al., U.S. Pat. No. 6,432,986 to Levin, PCT Publication WO 99/03473 to Levin, U.S. Pat. No. 6,491,940 to Levin, US Patent Application 2003/0133877 to Levin, and PCT Publication WO 00/44432 to Levin, US Patent Application 2001/0004644 to Levin, PCT Publication WO 01/43733 to Levin, U.S. Pat. No. 4,867,164 to Zabara, U.S. Pat. Nos. 6,341,236 and 6,671,556 to Osorio et al., U.S. Pat. No. 6,671,555 to Gielen et al., U.S. Pat. No. 5,978,702 to Ward et al., U.S. Pat. No. 6,205,359 to Boveja, U.S. Pat. No. 6,470,212 to Weijand et al., U.S. Pat. No. 6,640,137 to MacDonald, U.S. Pat. No. 6,735,475 to Whitehurst et al., PCT Publication WO 01/97906 to whitehurst, U.S. Pat. No. 6,922,590 to Whitehurst, PCT Publication WO 05/062829 to Whitehurst et al., and US Patent Application Publication 2005/0154419 to Whitehurst et al.

The following references, which are incorporated herein by reference, may be useful:

Delepine L, Aubineau P, "Plasma protein extravasation induced in the rat dura mater by stimulation of the parasympathetic sphenopalatine ganglion," Experimental Neurology, 147, 389-400 (1997)

Hara H, Zhang Q J, Kuroyanagi T, Kobayashi S, "Parasympathetic cerebrovascular innervation: An anterograde tracing from the sphenopalatine ganglion in the rat," Neurosurgery, 32, 822-827 (1993)

Jolliet-Riant P, Tillement J P, "Drug transfer across the blood-brain barrier and improvement of brain delivery," Fundam. Clin. Pharmacol., 13, 16-25 (1999)

Kroll R A, Neuwelt E A, "Outwitting the blood brain barrier for therapeutic purposes: Osmotic opening and other means," Neurosurgery, 42, 1083-1100 (1998)

Sanders M, Zuurmond W W, "Efficacy of sphenopalatine ganglion blockade in 66 patients suffering from cluster headache: A 12-70 month follow-up evaluation," Journal of Neurosurgery, 87, 876-880 (1997)

Syelaz J, Hara H, Pinard E, Mraovitch S, MacKenzie E T, Edvinsson L, "Effects of stimulation of the sphenopalatine ganglion on cortical blood flow in the rat," Journal of Cerebral Blood Flow and Metabolism," 8, 875-878 (1988)

Van de Waterbeemd H, Camenisch G, Folkers G, Chretien J R, Raevsky O A, "Estimation of blood brain barrier crossing of drugs using molecular size and shape and h bonding descriptors," Journal of Drug Targeting," 6, 151-165, (1998)

Suzuki N, Hardebo J E, Kahrstrom J, Owman C, "Selective electrical stimulation of postganglionic cerebrovascular parasympathetic nerve fibers originating from the sphenopalatine ganglion enhances cortical blood flow in the rat," Journal of Cerebral Blood Flow and Metabolism, 10, 383-391 (1990)

Suzuki N, Hardebo J E, Kahrstrom J, Owman C H, "Effect on cortical blood flow of electrical stimulation of trigeminal cerebrovascular nerve fibres in the rat," Acta Physiol. Scand., 138, 307-315 (1990)

Major A, Silver W, "Odorants presented to the rat nasal cavity increase cortical blood flow," Chem. Senses, 24, 665-669 (1999)

Fusco B M, Fiore G, Gallo F, Martelletti P, Giacovazzo M, "'Capsaicin-sensitive' sensory neurons in cluster headache: pathophysiological aspects and therapeutic indications," Headache, 34, 132-137 (1994)

Lambert G A, Bogduk N, Goadsby P J, Duckworth J W, Lance J W, "Decreased carotid arterial resistance in cats in response to trigeminal stimulation," Journal of Neurosurgery, 61, 307-315 (1984)

Silver W L, "Neural and pharmacological basis for nasal irritation," in Tucker W G, Leaderer B P, Mølhave L, Cain W S (eds), Sources of Indoor Air Contaminants, Ann. NY Acad. Sci., 641, 152-163 (1992)

Silver W, "Chemesthesis: the burning questions," ChemoSense, Vol. 2, 1-2 (1999)

Devoghel J C, "Cluster headache and sphenopalatine block," Acta Anaesthesiol Belg., 32(1):101-7 (1981)

Branston N M, "The physiology of the cerebrovascular parasympathetic innervation," British Journal of Neurosurgery 9:319-329 (1995)

Branston N M et al., "Contribution of cerebrovascular parasympathetic and sensory innervation to the short-term control of blood flow in rat cerebral cortex," J Cereb Blood Flow Metab 15(3):525-31 (1995)

Toda N et al., "Cerebral vasodilation induced by stimulation of the pterygopalatine ganglion and greater petrosal nerve in anesthetized monkeys," Neuroscience 96(2):393-398 (2000)

Seylaz J et al., "Effect of stimulation of the sphenopalatine ganglion on cortical blood flow in the rat," J Cereb Blood Flow Metab 8(6):875-8 (1988)

Nollet H et al., "Transcranial magnetic stimulation: review of the technique, basic principles and applications," The Veterinary Journal 166:28-42 (2003)

Van Gijn J et al., "Subarachnoid haemorrhage: diagnosis, causes and management," Brain 124:249-278 (2001)

Goadsby P J et al., "Effect of stimulation of trigeminal ganglion on regional cerebral blood flow in cats," Am J Physiol 22:R270-R274 (1987)

Walters B B et al., "Cerebrovascular projections from the sphenopalatine and otic ganglia to the middle cerebral artery of the cat," Stroke 17:488-494 (1986)

Suzuki N et al., "Trigeminal fibre collaterals storing substance P and calcitonin gene-related peptide associate with ganglion cells containing choline acetyltransferase and vasoactive intestinal polypeptide in the sphenopalatine ganglion of the rat. An axon reflex modulating parasympathetic ganglionic activity?" Neuroscience 30:595-604 (1989)

Roth B J et al., "In vitro evaluation of a 4-leaf coil design for magnetic stimulation of peripheral nerve," Electroencephalography and Clinical Neurophysiology 93:68-74 (1994)

Zhang R et al., "A nitric oxide donor induces neurogenesis and reduces functional deficits after stroke in rats," Ann Neurol 50:602-611 (2001)

Ziche M et al., "Nitric oxide and angiogenesis," J Neurooncol 50:139-148 (2000)

Kawamata T et al., "Intracisternal basic fibroblast growth factor (bFGF) enhances behavioral recovery following focal cerebral infarction in the rat," J Cereb Blood Flow Metab 16:542-547 (1996)

Zhang Z G et el., "VEGF enhances angiogenesis and promotes blood-brain barrier leakage in the ischemic brain," J Clin Invest 106:829-838 (2000)

Sun Y et al., "Neuronal nitric oxide synthase and ischemia-induced neurogenesis," J Cereb Blood Flow Metab 25(4): 485-92 (2005)

Zhang F et al., "Nitric oxide donors increase blood flow and reduce brain damage in focal ischemia: evidence that nitric oxide is beneficial in the early stages of cerebral ischemia," J Cereb Blood Flow Metab 14(2):217-26 (1994)

Beridze M et al., "Effect of nitric oxide initial blood levels on erythrocyte aggregability during 12 hours from ischemic stroke onset," Clin Hemorheol Microcirc 30(3-4):403-6 (2004)

Davis S M et al., "Advances in penumbra imaging with MR," Cerebrovasc Dis 17 Suppl 3:23-7 (2004)

Phan T G et al., "Salvaging the ischaemic penumbra: more than just reperfusion?" Clin Exp Pharmacol Physiol 29(1-2):1-10 (2002)

Gressens P et al., "Neuroprotection of the developing brain by systemic administration of vasoactive intestinal peptide derivatives," J Pharmacol Exp Ther 288 (3):1207-13 (1999)

Zhang R et al., "Nitric oxide enhances angiogenesis via the synthesis of vascular endothelial growth factor and cGMP after stroke in the rat," Circ Res 21; 92(3):308-13 (2003)

de la Torre J C, "Vascular basis of Alzheimer's pathogenesis," Ann NY Acad Sci 977:196-215 (2002)

Roman G C, "Cholinergic dysfunction in vascular dementia," Curr Psychiatry Rep 7(1):18-26 (2005)

Tony J F L, "Nitric oxide and the cerebral vascular function," J Biomed Sci 7:16-26 (2000)

Pluta R M, "Delayed cerebral vasospasm and nitric oxide: review, new hypothesis, and proposed treatment," Pharmacol Ther 105(1):23-56 (2005)

Sandgren K et al., "Vasoactive intestinal peptide and nitric oxide promote survival of adult rat myenteric neurons in culture," J Neurosci Res 72(5):595-602 (2003)

Laude K et al., "NO produced by endothelial NO synthase is a mediator of delayed preconditioning-induced endothelial protection," Am J Physiol Heart Circ Physiol 284(6): H2053-60 (2003) (Epub 2003 Jan. 9)

Khan M et al., "S-Nitrosoglutathione reduces inflammation and protects brain against focal cerebral ischemia in a rat model of experimental stroke," J Cereb Blood Flow Metab 25(2):177-92 (2005)

Molloy J et al., "S-nitrosoglutathione reduces the rate of embolization in humans," Circulation 98(14):1372-5 (1998)

Schmid-Elsaesser R et al., "A critical reevaluation of the intraluminal thread model of focal cerebral ischemia. Evidence of inadvertent premature reperfusion and subarachnoid hemorrhage in rats by laser-Doppler flowmetry," Stroke 29:2162-2170 (1998)

Zausinger V S et al., "Neurological impairment in rats after transient middle cerebral artery occlusion: a comparative study under various treatment paradigms," Brain Research 863(1-2):94-105 (2000)

Hunter A J et al., "To what extent have functional studies of ischemia in animals been useful in the assessment of potential neuroprotective agents?" Trends Pharmacol Sci 19:59-66 (1998)

Varghese et al., "Endoscopic transnasal neurolytic sphenopalatine ganglion block for head and neck cancer pain," J Laryngol Otol 115(5):385-7 (2001)

Hotta H et al., "Effects of stimulating the nucleus basalis of Meynert on blood flow and delayed neuronal death following transient ischemia in rat cerebral cortes," Jap J Phys 52:383-393 (2002)

Reis D J et al., "Electrical stimulation of cerebellar fastigial nucleus reduces ischemic infarction elicited by middle cerebral artery occlusion in rat," J Cereb Blood Flow Metab 11(5):810-8 (1991)

Matsui T et al., "The effects of cervical spinal cord stimulation (cSCS) on experimental stroke," Pacing Clin Electrophysiol 12(4 Pt 2):726-32 (1989)

Segher O et al., "Spinal cord stimulation reducing infract volume in model of focal cerebral ischemia in rats," J Neurosurg 99(1):131-137 (2003)

SUMMARY OF THE INVENTION

In an embodiment of the present invention, an oral appliance is provided that is adapted to be brought into contact with a mucous membrane of a palate of an oral cavity of a subject. The appliance comprises one or more electrodes, which are driven to apply transmucosal electrical stimulation to nerve fibers within or immediately above the mucous membrane, which fibers directly innervate an SPG of the subject. Typically, but not necessarily, such stimulation is performed while the subject is under general anesthesia or sedation. Such transmucosal stimulation may require less current than the transcutaneous stimulation described hereinabove.

In some embodiments of the present invention, a neural stimulation system comprises an implantable neural stimulator, an oral element, and an external control unit. The neural stimulator comprises an elongated support element, one or more electrodes fixed to the support element in a vicinity of a distal end thereof, and a wireless coupling element physically attached to the support element, e.g., in a vicinity of a proximal end thereof. The stimulator is adapted to be passed through a greater palatine foramen of a palate of an oral cavity of a subject into a greater palatine canal, such that the electrodes are brought into a vicinity of a sphenopalatine ganglion (SPG). For some applications, the stimulator comprises a locking element, which is adapted to hold the stimulator in place after implantation.

In some embodiments of the present invention, the distal end of the support element comprises a surgical punch, which enables the stimulator to be passed through the palate in a minimally-invasive procedure, without requiring a prior surgical incision in the mucosa. The wireless coupling element is sufficiently small so as to be able to pass through the punch incision without requiring the incision to be surgically enlarged. The use of the punch to insert the stimulator, rather than a more complicated surgical procedure, generally allows the stimulator to be quickly implanted in the subject.

The oral element of the system is adapted to be placed in the oral cavity, e.g., in a vicinity of or in contact with the roof of the oral cavity or the alveolar process of the maxilla, in a vicinity of the implanted wireless coupling element of the stimulator. The oral element comprises a power source, such as a rechargeable or disposable battery, and at least one wireless coupling element. The wireless coupling element of the oral element is adapted to wirelessly transmit energy to the wireless coupling element of the stimulator, for powering the stimulator. For some applications, the wireless coupling element of the oral element is additionally configured to transmit and/or receive data to/from the wireless coupling element of the stimulator. For some applications, the oral element transmits/receives data to/from the external control unit. Alternatively, the stimulator transmits/receives data directly to/from the external control unit.

In some embodiments of the present invention, a neural stimulation system comprises an implantable neural stimulator and an external control unit. The neural stimulator comprises an elongated support element, one or more electrodes fixed to the support element in a vicinity of a distal end thereof, and an implantable antenna coupled to the support element in a vicinity of a proximal end thereof. The support element is adapted to be passed through a palate of an oral cavity of a subject into a greater palatine canal, such that the electrodes are brought into a vicinity of a SPG. For some applications, the implantable antenna comprises a submucosal antenna comprising a thin, flexible sheet comprising at least one coil. The submucosal antenna is adapted to be implanted in the roof of the oral cavity between the oral mucosa and the palate, e.g., the hard palate, and to conform to the shape of the palate. For other applications, the implantable antenna comprises a coil antenna, which is coiled around at least a portion of the support element. In these embodiments, the system typically lacks an oral element. Instead, the external control unit is adapted to transmit power directly (typically as radiofrequency (RF) energy) to the submucosal antenna of the stimulator, and to transmit and/or receive data directly to/from the submucosal antenna. Typically, the external control unit is adapted to be placed in a vicinity of a head of the subject, such as in a vicinity of an ear of the subject, e.g., coupled to the ear.

In some embodiments of the present invention, the one or more electrodes of the stimulator comprise an array of electrodes, at least a portion of which are adapted to be separately activatable. After the stimulator has been implanted, the stimulation system uses a calibration algorithm to activate, during a plurality of calibration periods, respective different sets of one or more of the electrodes, in order to determine which set's activation causes a level of stimulation of the SPG closest to a desired level. Use of such an algorithm generally obviates the need to adjust the location of the stimulator after it has been implanted. For some applications, the level of stimulation of the SPG is determined by receiving feedback directly from the SPG, or from other neural tissue in a vicinity of the SPG, i.e., by using at least a portion of the electrodes to directly measure a level of stimulation of the SPG or the other neural tissue at or in a vicinity of the site(s) of the stimulation by the electrodes. Alternatively, the level of stimulation of the SPG is determined by assessing an indirect physiological parameter of the subject related to the level of SPG stimulation, such as cerebral blood flow (CBF).

In some embodiments of the present invention, the elongated support element of the stimulator has a length of between about 1.8 and about 4 cm, such as between about 1.8 cm and about 3 cm, e.g., between about 2.6 and about 3 cm, such as about 2.8 cm, and/or has a curvature that follows that of the greater palatine canal.

For some applications, treatment with the systems described herein is applied as soon as possible after diagnosis of the condition, such as in an emergency room or wherever the subject happens to be. For other applications, the system is appropriate for longer-term treatment, such as for modulating the permeability of the BBB, modulating cerebral blood flow (CBF), rehabilitation after brain events, or prevention and/or treatment of epilepsy. For some applications, the stimulator is adapted to be implanted for at least one week, e.g., at least one month, while for other applications, the stimulator is adapted to be implanted for less than one week, e.g., less than one day.

In some embodiments of the present invention, an electrical stimulator drives current into at least one "modulation target site" (MTS), as defined hereinbelow. Typically, the stimulator drives the current in order to control and/or modify SPG-related behavior, e.g., in order to induce changes in cerebral blood flow and/or to modulate permeability of the blood-brain barrier (BBB). Concurrently with or after placement of the stimulator near or in contact with an MTS, at least one physiological indicator of cerebral blood flow (CBF) is observed or measured. Optimization of placement of the stimulator onto the appropriate neural structure is performed by activating the stimulator, and generally simultaneously monitoring CBF while manipulating the placement of the stimulator so as to increase or decrease CBF, as appropriate. Alternatively or additionally, a similar optimization process is performed, either during or after implantation of the stimulator, to determine parameters of the applied current that achieve a desired effect, as indicated by CBF.

In the present patent application, a "modulation target site" (MTS) consists of:
- an SPG (also called a pterygopalatine ganglion);
- a nerve of the pterygoid canal (also called a vidian nerve), such as a greater superficial petrosal nerve (a preganglionic parasympathetic nerve) or a lesser deep petrosal nerve (a postganglionic sympathetic nerve);
- a greater palatine nerve;
- a lesser palatine nerve;
- a sphenopalatine nerve;
- a communicating branch between the maxillary nerve and the sphenopalatine ganglion;
- an otic ganglion;
- an afferent fiber going into the otic ganglion;
- an efferent fiber going out of the otic ganglion; or
- an infraorbital nerve.

It is to be appreciated that while some embodiments of the invention are generally described herein with respect to electrical transmission of power and electrical modulation of tissue, other modes of energy transport may be used as well. Such energy includes, but is not limited to, direct or induced electromagnetic energy, radiofrequency (RF) transmission, mechanical vibration, ultrasonic transmission, optical power, and low power laser energy (via, for example, a fiber optic cable).

It is further to be appreciated that whereas some embodiments of the present invention are described with respect to application of electrical currents to tissue, this is to be understood in the context of the present patent application and in the claims as being substantially equivalent to applying an electrical field, e.g., by creating a voltage drop between two electrodes.

There is further provided, in accordance with an embodiment of the present invention, apparatus for modifying a property of a brain of a subject, including:
at least one electrode, adapted to be positioned in a vicinity of a mucous membrane of a palate of an oral cavity of the subject; and
a control unit, adapted to drive the electrode to apply an electrical current to the mucous membrane, and to configure the current to be capable of inducing an increase in permeability of a blood-brain barrier (BBB) of the subject.

For some applications, the control unit is adapted to configure the current to have a magnitude sufficient to activate a sphenopalatine ganglion (SPG) of the subject via nerve fibers in physical contact with the mucous membrane.

For some applications, the control unit is adapted to configure the current to increase the permeability of the BBB to a magnitude sufficient to treat a condition of the subject. Alternatively or additionally, the control unit is adapted to configure the current to increase the permeability of the BBB to a magnitude sufficient to perform a diagnosis of a condition of the subject.

There is still further provided, in accordance with an embodiment of the present invention, apparatus for modifying a property of a brain of a subject, including:
at least one electrode, adapted to be positioned in a vicinity of a mucous membrane of a palate of an oral cavity of the subject; and
a control unit, adapted to drive the electrode to apply an electrical current to the mucous membrane, and to configure the current to be capable of inducing an increase in cerebral blood flow (CBF) of the subject.

For some applications, the control unit is adapted to configure the current to have a magnitude sufficient to activate a sphenopalatine ganglion (SPG) of the subject via nerve fibers in physical contact with the mucous membrane.

For some applications, the control unit is adapted to configure the current to increase the CBF to a magnitude sufficient to treat a condition of the subject.

There is additionally provided, in accordance with an embodiment of the present invention, a method for modifying a property of a brain of a subject, including applying an electrical current to a mucous membrane of a palate of an oral cavity of the subject, the current capable of inducing an increase in permeability of a blood-brain barrier (BBB) of the subject.

In an embodiment, the method includes administering a sedative to the subject in conjunction with applying the current. Alternatively or additionally, the method includes administering an anesthetic to the subject in conjunction with applying the current.

In an embodiment, the method includes performing a diagnostic activity with respect to a condition of the subject, in conjunction with the increase in permeability of the BBB.

There is yet additionally provided, in accordance with an embodiment of the present invention, a method for modifying a property of a brain of a subject, including applying an electrical current to a mucous membrane of a palate of an oral cavity of the subject, the current capable of inducing an increase in cerebral blood flow (CBF) of the subject.

There is therefore provided, in accordance with an embodiment of the present invention, apparatus for application to a subject, including:
an elongated support element having a length of between 1.8 cm and 4 cm, and having proximal and distal ends;
one or more electrodes fixed to the support element in a vicinity of the distal end thereof, and adapted to apply an electrical current to a sphenopalatine ganglion (SPG) of the subject;
a receiver, fixed to the support element, and electrically coupled to the electrodes; and
a wireless transmitter, adapted to be placed in an oral cavity of the subject, and to be wirelessly coupled to the receiver.

For some applications, the wireless transmitter is adapted to be electromagnetically coupled to the receiver, or wirelessly coupled to the receiver via ultrasound. Alternatively, the receiver is adapted to be wireless coupled to the wireless transmitter by induction. For some applications, the electrodes are adapted to apply the current using only power received by the receiver from the wireless transmitter.

For some applications, the apparatus includes an oral appliance, adapted to be fixed to the transmitter, and shaped so as to define a surface that fits closely to a roof of the oral cavity. Alternatively, the apparatus includes an oral appliance, adapted to be fixed to the transmitter, and adapted to be coupled to a tooth of the subject, and/or adapted to be coupled to gingival covering an alveolar process of the subject.

For some applications, the apparatus includes an oral appliance, which includes: a capsule, which is configured to be placed and held between an alveolar process and an inner surface of a cheek of the subject; the transmitter; and an elongated coupling element, which couples the transmitter to the capsule. For some applications, the transmitter is adapted to be implanted in a tooth of the subject. For some applications, at least a portion of the receiver is adapted to be positioned between mucosa and a hard palate of the subject. Alternatively, at least a portion of the receiver is adapted to be positioned between mucosa and an alveolar process of a maxilla of the subject.

For some applications, the apparatus includes one or more electrode leads, which electrically couple the receiver to the electrodes, and which serve as the support element. For some applications, the distal end of the support element includes a surgical punch.

In an embodiment, the apparatus includes an external control unit, adapted to be placed outside of a head of the subject, which includes a control unit wireless coupling element, which is adapted to wirelessly transmit data from the control unit to the receiver.

For some applications, the electrodes include exactly one cathode and exactly one anode, and a closest distance between the cathode and the anode is greater than a closest distance between any portion of the cathode and any portion of the SPG when the electrodes are positioned in a vicinity of the SPG.

For some applications, the support element, electrodes, and receiver are adapted to be implanted in the subject for at least one week. Alternatively, the support element, electrodes, and receiver are adapted to be implanted in the subject for less than one day.

For some applications, the support element is sufficiently rigid to enable insertion of the support element into a body of the subject by pushing from a vicinity of the proximal end of the support element.

For some applications, the support element has a curvature that follows that of a greater palatine canal of the subject.

In an embodiment, the receiver is fixed to the support element in a vicinity of the proximal end of the support element. For some applications, the apparatus includes a circuit module, which is fixed to the proximal end of the support element, and which includes a printed circuit board and the receiver. For some applications, the circuit module includes one or more layers of coating applied thereto.

For some applications, the support element is folded in a vicinity of the proximal end of the support element, at an angle approximately equal to an angle between a greater palatine canal of the subject and a hard palate of the subject in a vicinity of a greater palatine foramen of a subject, and the circuit module is adapted to be placed submucosally against a lower surface of the hard palate.

Alternatively, the proximal end of the support element is fixed to the circuit module such that an angle between the support element and a surface of the circuit module is approximately equal to an angle between a greater palatine canal of the subject and a hard palate of the subject in a vicinity of a greater palatine foramen of a subject, and the circuit module is adapted to be placed submucosally against a lower surface of the hard palate. For some applications, the proximal end of the support element is fixed to the circuit module in a vicinity of a center of the surface of the circuit module, or in a vicinity of an edge of the surface of the circuit module.

For some applications, the proximal end of the support element is fixed to the circuit module in a vicinity of an edge of the circuit module, and the circuit module is adapted to be placed submucosally against an alveolar process of a maxilla of the subject.

In an embodiment, the apparatus includes: an external control unit, adapted to be placed outside of a head of the subject, the external control unit including a control unit wireless coupling element; a support element wireless coupling element, coupled to the support element; and circuitry, coupled to the support element, and adapted to drive the wireless coupling element to wirelessly transmit feedback information to the external control unit. For some applications, the support element wireless coupling element and the receiver include a common transducer element.

In an embodiment, the apparatus includes: an oral element, which includes the wireless transmitter; an external driver, which includes a power source and circuitry, and which is adapted to be placed outside a body of the subject; and one or more wires which electrically couple the external driver to the oral element. For some applications, the external driver is adapted to be physically coupled to the body of the subject. For some applications, the apparatus includes an external control unit, which is adapted to be placed outside the body of the subject, and which is coupled to the external driver.

In an embodiment, the apparatus includes an oral element, which includes the wireless transmitter and oral element circuitry coupled to the wireless transmitter; and a power source, adapted to provide power to the wireless transmitter and circuitry. For some applications, the oral element includes the power source. Alternatively, the power source is adapted to be placed outside a body of the subject, and to be coupled to the oral element. For some applications, the apparatus includes receiver circuitry, which is coupled to the support element and the receiver, and the oral element circuitry is adapted to drive the wireless transmitter to transmit energy that does not include a stimulation waveform for application by the electrodes, the receiver is adapted to receive the energy, and the receiver circuitry is adapted to generate the stimulation waveform using the energy, and to drive the electrodes to apply the stimulation waveform to the SPG.

For some applications, the apparatus includes receiver circuitry, which is coupled to the support element and the receiver, and the oral element circuitry is adapted to drive the wireless transmitter to transmit energy that includes a stimulation waveform for application by the electrodes, the receiver is adapted to receive the energy, and the receiver circuitry is adapted to drive the electrodes to apply the stimulation waveform to the SPG.

For some applications, the oral element is adapted to be fixed to a roof of the oral cavity. Alternatively, the oral element is adapted to temporarily placed against the roof of the oral cavity, without being fixed thereto.

For some applications, the apparatus includes an external control unit, adapted to be placed outside of a head of the subject, the external control unit including a control unit wireless coupling element, which is adapted to wirelessly transmit data from the control unit to the oral element, and the oral element is adapted to wirelessly transmit the received data to the receiver. For some applications, the oral element is adapted to wirelessly transmit feedback information to the external control unit.

In an embodiment, the support element has a length of between 1.8 and 3 cm, such as between 2.6 and 3 cm.

In an embodiment, at least a portion of the support element is adapted to be placed in a greater palatine canal of the subject. For some applications, the support element includes a lock, adapted to hold the support element in place after insertion thereof into the greater palatine canal. For some applications, the support element is adapted to be inserted into the greater palatine canal such that no portion of the support element protrudes into the oral cavity. For example, the receiver may be adapted to be contained entirely within the greater palatine canal when the support element is inserted into the greater palatine canal. For some applications, the receiver includes at least one coil that is coiled around at least a portion of the support element. For some applications, the at least one coil includes a plurality of coils which are oriented in a plurality of respective orientations.

For some applications, the apparatus includes circuitry adapted to measure, using at least one of the electrodes, a level of stimulation induced by the applied current, such as a level of stimulation of the SPG.

For some applications, the one or more electrodes include a plurality of electrodes, and the apparatus includes circuitry adapted to perform a calibration procedure by activating, during a plurality of calibration periods, respective different sets of one or more of the electrodes. For some applications, the circuitry is adapted to measure, during each of the calibration periods, using at least one of the electrodes, an indication of a level of stimulation induced by the activation of the respective set of electrodes, such as a level of stimulation of the SPG.

There is further provided, in accordance with an embodiment of the present invention, apparatus for application to a subject, including:

one or more electrodes adapted to apply an electrical current to tissue of the subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve;

a receiver, electrically coupled to the one or more electrodes; and a wireless transmitter, adapted to be placed in an oral cavity of the subject, and to be wirelessly coupled to the receiver.

In an embodiment, the tissue includes the SPG, and the one or more electrodes are adapted to apply the current to the SPG.

For some applications, the wireless transmitter is adapted to be electromagnetically coupled to the receiver, or wirelessly coupled to the receiver via ultrasound. Alternatively, the receiver is adapted to be wirelessly coupled to the wireless transmitter by induction.

For some applications, the apparatus includes an oral appliance, adapted to be fixed to the transmitter, and shaped so as to define a surface that fits closely to a roof of the oral cavity.

There is also provided, in accordance with an embodiment of the present invention, apparatus for application to a subject, including:

an elongated support element adapted to be placed within a greater palatine canal of the subject, sized to extend from a palate of the subject to a sphenopalatine ganglion (SPG) of the subject, and having distal and proximal ends; and one or more electrodes fixed to the support element in a vicinity of the distal end thereof; and a control unit, coupled to the electrodes, and adapted to drive the electrodes to apply an electrical current to the SPG.

In an embodiment, the support element is adapted to have a length that is adjustable during an implantation procedure. For some applications, the support element includes at least two portions that are telescopically coupled to one another. For some applications, the apparatus includes a sleeve, which surrounds a portion of the support element. For some applications, a portion of the support element is shaped so as to define one or more accordion pleats. For some applications, the apparatus includes one or more electrode leads coupled to the electrodes, which leads serve as the support element and are accordion-pleated, a portion of which leads are helically wound so as to form a spring, or which leads are shaped so as to define at least one omega-shaped portion.

In an embodiment, the support element includes a support element electrical contact in a vicinity of the proximal end thereof, the control unit includes a control unit electrical contact, and the control unit is adapted to be placed in an oral cavity of the subject such that the control unit electrical contact is brought into physical contact with the support element electrical contact, thereby coupling the control unit to the electrodes. For some applications, the control unit is adapted to temporarily placed against a roof of the oral cavity, without being fixed thereto. For some applications, the control unit is adapted to be fixed to a roof of the oral cavity. For some applications, the support element electrical contact is adapted to be in sealed contact with mucosa of the subject. Alternatively or additionally, the support element electrical contact includes a matrix, which is adapted to promote mucosal tissue growth therein.

In an embodiment, the apparatus includes a receiver, which is fixed to the support element; and a wireless transmitter, which is coupled to the control unit, and which is adapted to be wirelessly coupled to the receiver, thereby coupling the control unit to the electrodes. For some applications, the wireless transmitter is adapted to be placed in an oral cavity of the subject. Alternatively, the wireless transmitter is adapted to be placed outside of a head of the subject. For some applications, the apparatus includes an autonomically-powered power supply physically coupled to the support element, which is adapted to provide power for the electrodes, and the control unit is adapted to wirelessly transmit data to the receiver.

There is additionally provided, in accordance with an embodiment of the present invention, apparatus including an implantable neural stimulator, which includes:

one or more electrodes adapted to be placed in a vicinity of a greater palatine foramen of a subject; and a control unit, coupled to the electrodes, and adapted to drive the electrodes to apply an electrical current to a greater palatine nerve of the subject.

For some applications, the electrodes are adapted to be placed within 5 mm of the greater palatine foramen. For some applications, the electrodes are adapted to be contained entirely within a greater palatine canal of the subject. For some applications, at least a portion of the electrodes is adapted to be located between mucosa and a palate of the subject.

There is yet additionally provided, in accordance with an embodiment of the present invention, apparatus including an implantable neural stimulator, which includes:

one or more electrodes adapted to apply an electrical current to tissue of a subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve;

an implantable submucosal antenna, which includes at least one coil, and is adapted to be implanted between oral mucosa and a palate of the subject; and one or more electrode leads, which electrically couple the submucosal antenna to the electrodes.

In an embodiment, the tissue includes the SPG, and the one or more electrodes are adapted to apply the current to the SPG.

In an embodiment, the submucosal antenna includes a flexible sheet, which includes the at least one coil.

For some applications, the apparatus includes an external driver, which includes a power source and circuitry, which is adapted to be placed outside a body of the subject, and which is adapted to be wirelessly coupled to the submucosal antenna; and an external control unit, which is adapted to be placed outside the body of the subject, and which is coupled to the external driver.

In an embodiment, the stimulator includes an elongated support element having proximal and distal ends, which is adapted to be inserted into a greater palatine canal of the subject, and the one or more electrodes are coupled to the support element in a vicinity of the distal end, and the submucosal antenna is coupled to the support element in a vicinity of the proximal end. For some applications, the support element has a length of between 2.6 cm and 3 cm. For some applications, the support element is adapted to have a length that is adjustable during an implantation procedure.

In an embodiment, the apparatus includes a control unit, adapted to be wirelessly coupled to the submucosal antenna. For some applications, the control unit is adapted to transmit power and data to the submucosal antenna, and the stimulator is adapted to use the power to generate a stimulation waveform at least in part responsively to the received data, and to drive the one or more electrodes to apply the stimulation waveform. For some applications, the control unit is adapted to be placed externally to a body of the subject, such as in a vicinity of a head of the subject, e.g., in a vicinity of an ear of the subject.

There is still additionally provided, in accordance with an embodiment of the present invention, apparatus including an implantable neural stimulator, which includes:

a plurality of electrodes adapted to apply an electrical current to a site of a subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve; and a control unit, coupled to the electrodes, and adapted to perform a calibration procedure by activating, during a plurality of calibration periods, respective different sets of one or more of the electrodes.

For some applications, the control unit is adapted to be placed externally to a body of the subject, and to be wirelessly coupled to the electrodes.

In an embodiment, the control unit is adapted to receive, during each of the calibration periods, an indication of a level of stimulation induced by the activation of the respective set of electrodes, such as a level of stimulation of the site. For some applications, the control unit is adapted to select the set of electrodes the activation of which induced the level of stimulation nearest a desired level of stimulation.

For some applications, the control unit is adapted to receive the indication of the level of stimulation, e.g., of the site, by using at least a portion of the electrodes to measure the level of stimulation. For some applications, the control unit is adapted to measure, using the at least a portion of the electrodes, an electric field of nervous tissue, e.g., of the site, induced by the activation of the respective set of electrodes. For some applications, the at least a portion of the electrodes includes one or more of the electrodes of the respective set of electrodes. For some applications, the at least a portion of the electrodes includes one or more of the electrodes positioned in a vicinity of the electrodes of the respective set of electrodes.

For some applications, the indication includes an indirect physiological parameter of the subject related to the level of the stimulation, and the control unit is adapted to receive the indirect physiological parameter during each of the calibration periods. For some applications, the indirect physiological parameter includes an indication of cerebral blood flow (CBF) of the subject, and the control unit is adapted to receive the indication of CBF. For some applications, the indirect physiological parameter includes an indication of blood-brain barrier (BBB) permeability of the subject, and the control unit is adapted to receive the indication of BBB permeability. For some applications, the apparatus includes a device adapted to measure the indirect physiological parameter, and the control unit is adapted to receive the indirect physiological parameter measured by the device.

In an embodiment, the site includes the SPG, and the electrodes are adapted to apply the current to the SPG. For some applications, the stimulator includes an elongated support element having a distal end, and adapted to be inserted into a greater palatine canal of the subject via a palate of the subject, and the electrodes are coupled to the support element in a vicinity of the distal end.

There is still further provided, in accordance with an embodiment of the present invention, apparatus including an implantable neural stimulator, which includes:

a set of one or more electrodes adapted to be placed in a vicinity of a site of a subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve; and a control unit, coupled to the set of electrodes, and adapted to:

drive at least one of the electrodes to apply an electrical current to the site, and using at least one of the electrodes, measure a level of stimulation induced by the applied current.

In an embodiment, the level of stimulation includes a level of stimulation of the site induced by the applied current, and the control unit is adapted to measure the level of stimulation of the site, using the at least one of the electrodes.

In an embodiment, the site includes the SPG, and the electrodes are adapted to be placed in the vicinity of the SPG.

For some applications, the control unit is adapted to measure the level of stimulation using at least one of the at least one of the electrodes that applies the current to the site. For some applications, the control unit is adapted to measure the level of stimulation using at least one of the electrodes positioned in a vicinity of the at least one of the electrodes that applies the current to the site. For some applications, the control unit is adapted to measure, using the at least one of the electrodes, an electric field of nervous tissue, e.g., of the site, induced by the applied current.

There is also provided, in accordance with an embodiment of the present invention, apparatus including an implantable neural stimulator, which includes:

an elongated support element having a length of between 2.6 cm and 3 cm, having a distal end, and including, at the distal end, a surgical punch adapted to facilitate insertion of the support element through mucosa of the subject into a greater palatine canal of a subject, via a greater palatine foramen of the subject; and one or more electrodes fixed to the support element in a vicinity of the distal end thereof, and adapted to apply an electrical current to a sphenopalatine ganglion (SPG) of the subject.

For some applications, the support element includes a lock, adapted to hold the support element in place after insertion thereof into the greater palatine canal.

There is further provided, in accordance with an embodiment of the present invention, apparatus including an implantable neural stimulator, which includes:

an elongated support element having a length of between 2.6 cm and 3 cm, having a distal end, and adapted to be placed in a greater palatine canal of a subject;

one or more electrodes fixed to the support element in a vicinity of the distal end thereof, and adapted to apply an electrical current to a sphenopalatine ganglion (SPG) of the subject; and a needle shaped so as to define a sharp distal end and a bore, which bore is adapted to hold the support element and the electrodes during insertion of the support element and the electrodes into the greater palatine canal, and to be withdrawn from the greater palatine canal thereafter, leaving the support element and electrodes in the greater palatine canal.

For some applications, the support element includes a lock, adapted to hold the support element in place after insertion thereof into the greater palatine canal.

There is still further provided, in accordance with an embodiment of the present invention, apparatus including an implantable neural stimulator, which includes:

one or more electrodes adapted to apply an electrical current to tissue of a subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve;

a receiver, electrically coupled to the one or more electrodes;

an oral appliance, which includes:
a capsule, which is configured to be placed and held between an alveolar process and an inner surface of a cheek of the subject;
a wireless transmitter, adapted to be wirelessly coupled to the receiver; and
an elongated coupling element, which couples the transmitter to the capsule; and
a power source, electrically coupled to the wireless transmitter.

In an embodiment, the capsule includes the power source. Alternatively, the apparatus includes a cable, and the power source is adapted to be placed outside of a body of the subject, and is physically and electrically coupled to the capsule via the cable.

For some applications, the capsule is generally cylindrical. For some applications, the capsule includes a soft coating.

In an embodiment, the coupling element is configured such that the transmitter is positioned on a lingual side of teeth of the subject when the capsule is held between the alveolar process and the inner surface of the cheek. For some applications, the coupling element is configured to pass over an occlusal surface of one or more teeth of the subject. Alternatively, the coupling element is configured to pass around a distal surface of a most distal molar of the subject.

There is additionally provided, in accordance with an embodiment of the present invention, a method including:

inserting an elongated support element into a body of a subject, the element having a length of between about 1.8 cm and about 4 cm, and having proximal and distal ends;

wirelessly transmitting energy from within an oral cavity of the subject;

receiving the energy at the support element; and using the received energy, applying, from a vicinity of the distal end of the support element, an electrical current to a sphenopalatine ganglion (SPG) of the subject.

In an embodiment, inserting the support element includes:
preparing a submucosal surface on a hard palate of the subject;
inserting the support element into a greater palatine canal of the subject; and
placing a circuit module, which is fixed to the proximal end of the support element, against the prepared submucosal surface, and
receiving the energy at the support element includes receiving the energy at the circuit module.

In an embodiment, inserting the support element includes:
preparing a submucosal surface on an alveolar process of a maxilla of the subject;
inserting the support element into a greater palatine canal of the subject; and
placing a circuit module, which is fixed to the proximal end of the support element, against the prepared submucosal surface, and
receiving the energy at the support element includes receiving the energy at the circuit module.

There is yet additionally provided, in accordance with an embodiment of the present invention, a method including:

wirelessly transmitting energy from within an oral cavity of a subject;

receiving the energy; and using the received energy, applying an electrical current to tissue of the subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve.

There is also provided, in accordance with an embodiment of the present invention, a method including:

inserting an elongated support element into a greater palatine canal of the subject, such that the support element extends from a palate of the subject to a sphenopalatine ganglion (SPG) of the subject, the support element having a distal end; and applying, from a vicinity of the distal end, an electrical current to the SPG.

There is further provided, in accordance with an embodiment of the present invention, a method including applying an electrical current to a greater palatine nerve of a subject from a site in a vicinity of a greater palatine foramen of a subject.

There is still further provided, in accordance with an embodiment of the present invention, a method including:

implanting, between oral mucosa and a palate of the subject, a submucosal antenna that includes at least one coil;

wirelessly transmitting energy to the submucosal antenna;

receiving the energy at the submucosal antenna; and using the energy, applying an electrical current to tissue of a subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve.

There is additionally provided, in accordance with an embodiment of the present invention, a method including performing a calibration procedure by applying an electrical current to an anatomical site of a subject, during a plurality of calibration periods, from respective different sets of one or more stimulation sites in a vicinity of the anatomical site, the anatomical site selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve.

There is yet additionally provided, in accordance with an embodiment of the present invention, a method including:

placing a set of one or more electrodes in a vicinity of a site of a subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve;

driving at least one of the electrodes to apply an electrical current to the site; and using at least one of the electrodes, measuring a level of stimulation induced by the applied current.

There is also provided, in accordance with an embodiment of the present invention, a method including:

inserting, into a greater palatine canal of a subject, via a greater palatine foramen of the subject, an elongated support element having a length of between 2.6 cm and 3 cm and having a distal end, by using the distal end of the support element to punch an incision in mucosa of the subject; and applying, from a vicinity of the distal end of the support element, an electrical current to a sphenopalatine ganglion (SPG) of the subject.

There is further provided, in accordance with an embodiment of the present invention, a method including:

placing an elongated support element, having a length of between 2.6 cm and 3 cm and having a distal end, into a bore of a needle shaped so as to define a sharp distal end;

inserting, into a greater palatine canal of a subject, the needle holding the support element;

withdrawing the needle from the greater palatine canal thereafter, leaving the support element in the greater palatine canal; and applying, from a vicinity of the distal end of the support element, an electrical current to a sphenopalatine ganglion (SPG) of the subject.

There is still further provided, in accordance with an embodiment of the present invention, a method including:

placing a capsule between an alveolar process and an inner surface of a cheek of a subject;

placing, in an oral cavity of the subject, a wireless transmitter coupled to the capsule by an elongated coupling element;

wirelessly transmitting energy from the wireless transmitter; and receiving the energy, and, using the received energy, applying an electrical current to tissue of the subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve.

There is additionally provided, in accordance with an embodiment of the present invention, apparatus including:

an instrument, adapted to detect an indication of cerebral blood flow (CBF) of a subject, and to generate a signal responsive thereto;

one or more electrodes, adapted to be placed in a vicinity of a site of the subject selected from a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve; and a control unit, adapted to:
receive the signal,
drive the one or more electrodes to apply a current to the site capable of inducing a change in the CBF, and
configure a parameter of the current responsively to the signal.

For some applications, the instrument includes a laser Doppler perfusion device, a transcranial Doppler ultrasonography device, a thermometer, or a near infrared spectroscopy (NIRS) device. Alternatively, the instrument includes an image sensor, adapted to image an eye of the subject, and the indication of CBF includes an indication of vasodilation of blood vessels of the eye. For some applications, the indication of vasodilation of the blood vessels of the eye includes a ratio of red to white in a sclera of the eye, and the instrument is adapted to determine the ratio.

There is yet additionally provided, in accordance with an embodiment of the present invention, a method including:

placing one or more electrodes in a vicinity of a site of a subject selected from a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve;

applying a current to the site capable of inducing a change in cerebral blood flow (CBF) of the subject;

detecting an indication of the CBF; and responsively to the indication, adjusting at least one of: a placement of the electrodes, and a parameter of the applied current.

The present invention will be more fully understood from the following detailed description of the embodiments thereof, taken together with the drawings, in which:

BRIEF DESCRIPTION OF THE DRAWINGS

FIGS. 7A-B are schematic illustrations of an oral element of the system of FIG. 1, in accordance with respective embodiments of the present invention;

FIG. 8 is a schematic illustration of an oral element of the system of FIG. 1 coupled to an oral appliance, in accordance with an embodiment of the present invention;

FIG. 9 is a schematic illustration of a contact-based energy transmission configuration of the system of FIG. 1, in accordance with an embodiment of the present invention;

FIG. 10 is a schematic illustration of a configuration of a contact of the configuration of FIG. 9, in accordance with an embodiment of the present invention;

FIG. 11A-B are schematic illustrations of energy and data transmission paths between components of the system of FIG. 1, in accordance with respective embodiments of the present invention;

FIG. 12 is a schematic illustration of another neural stimulation system, in accordance with an embodiment of the present invention;

FIG. 19 is a schematic illustration of a vasodilation measurement instrument, in accordance with an embodiment of the present invention;

FIG. 20 is a schematic illustration of a laser Doppler imaging (LDI) device, in accordance with an embodiment of the present invention;

FIG. 21 is a schematic illustration of a thermometer, in accordance with an embodiment of the present invention; and FIG. 22 is a schematic illustration of a transcranial Doppler ultrasonography device, in accordance with an embodiment of the present invention.

DETAILED DESCRIPTION OF THE INVENTION

Figure 1:
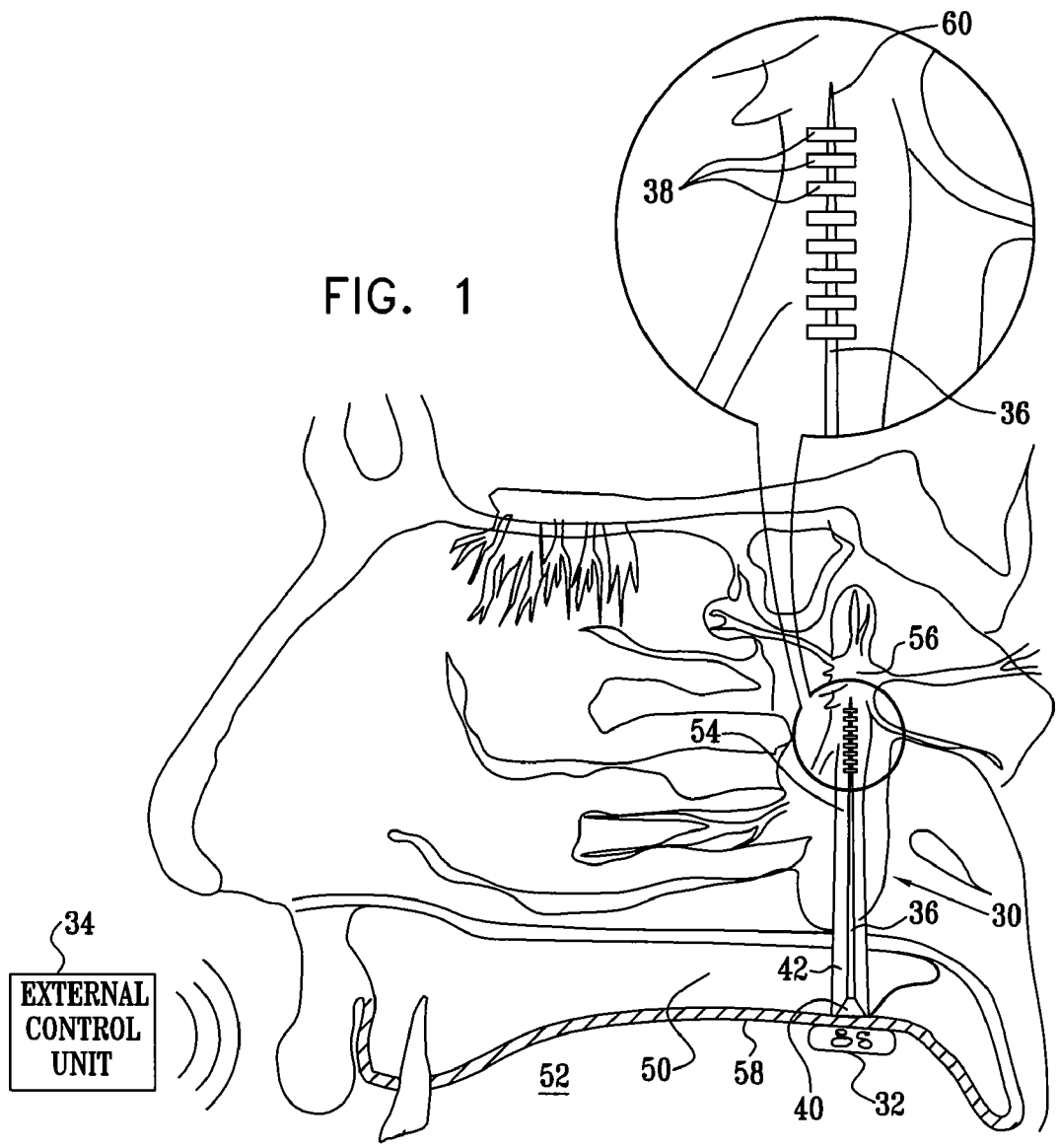
FIG. 1 is a schematic illustration of a neural stimulation system, in accordance with an embodiment of the present invention.

FIG. 1 is a schematic illustration of a neural stimulation system 20, in accordance with an embodiment of the present invention. System 20 typically comprises an implantable neural stimulator 30, an oral element 32, and an external control unit 34. Stimulator 30 comprises an elongated support element 36, one or more electrodes 38 fixed to the support element in a vicinity of a distal end thereof, and circuitry 40 coupled to the support element in a vicinity of a proximal end thereof. Circuitry 40 typically comprises a wireless coupling element (which typically comprises a coil), and additional elements, such as one or more rectifiers, capacitors, amplifiers, or filters. One or more leads (not shown in FIG. 1), which pass along, through, or around support element 36, couple electrodes 38 to circuitry 40. Alternatively, the leads function as the support element, i.e., the support element does not comprise any structural elements in addition to the leads. Further alternatively, the leads provide a substantial portion of the structural support of the support element, and the balance of the structural support is provided by other elements. For example, support element 36 may comprise the leads and a flexible sleeve surrounding the leads; the leads supply most of the structural support of the support element, while the sleeve allows smooth passage of the leads through the greater palatine canal. Circuitry 40 is shown schematically in FIG. 1; several more detailed configurations of the circuitry are described hereinbelow with reference to FIGS. 3A-B, 4A-B, and 5A-D.

Stimulator 30 is adapted to be passed through a greater palatine foramen 42 of a hard palate 50 of an oral cavity 52 of a subject into a greater palatine canal 54, such that electrodes 38 are brought into a vicinity of a sphenopalatine ganglion (SPG) 56. For some applications, the entire stimulator is contained within greater palatine canal 54, while for other applications, at least a portion of the circuitry and/or the support element are positioned submucosally in the oral cavity. For clarity of illustration, the greater and lesser palatine nerves, and the greater and less palatine arteries are not shown in the figures. During an implantation procedure, stimulator 30 is typically passed through greater palatine foramen 42 posterior to the greater palatine nerve and artery, which are manipulated into an anterior position within the canal.

For some applications, electrodes 38 apply a monophasic waveform to SPG 56, while for other applications, electrodes 38 apply a biphasic waveform. Alternatively or additionally, waveforms and/or stimulation techniques may be used that are described in one or more of the patent applications incorporated by reference hereinbelow, or waveforms and/or stimulation techniques may be used that are known in the art of neural stimulation.

For some applications, the distal end of support element 36 comprises a surgical punch 60, which is adapted to be passed through mucosa 58 and greater palatine foramen 42 without requiring a prior surgical incision in the mucosa, i.e., without requiring the use of a surgical knife or other tool. Circuitry 40 is sufficiently small so as to be able to pass through the punch incision without requiring the incision to be surgically enlarged.

For some applications, stimulator 30 comprises a locking element, such as in a vicinity of the proximal end thereof, which is adapted to hold the stimulator in place after insertion. For some applications, the locking element comprises a screw, which is adapted to couple the stimulator to the palate or the alveolar process of the maxilla. Alternatively or additionally, the locking element comprises a bonding agent, which is adapted to bond the stimulator to the palate, the alveolar process of the maxilla, or an internal surface of greater palatine canal 54.

Figure 2:
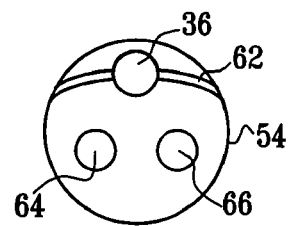
FIG. 2 is a schematic cross-sectional illustration of a spring-loaded locking element engaging the greater palatine canal, in accordance with an embodiment of the present invention.

Reference is made to FIG. 2, which is a schematic cross-sectional illustration of a spring-loaded locking element 62 engaging greater palatine canal 54, in accordance with an embodiment of the present invention. Locking element 62 applies lateral pressure on the interior surface of a portion of greater palatine canal 54 in a vicinity of foramen 42, thereby locking elongated support element 36 in place in the canal. Locking element 62 is configured so as to not interfere with a descending palatine artery 64 or a greater palatine nerve 66, both of which pass through greater palatine canal 54.

For some applications, support element 36 has a length of between about 1.8 and about 3 cm, such as between about 2.6 cm and about 3 cm, e.g., between about 2.6 and about 3 cm, such as about 2.8 cm, and has a curvature that follows that of the greater palatine canal. For some applications, support element 36 has a diameter at its widest portion of between about 1 and about 4 mm. For some applications, support element 36 comprises a tube. For some applications, support element 36 is semi-rigid (i.e., it generally keeps its original shape during a placement procedure). For example, support element 36 may be sufficiently rigid to enable insertion of the support element into a body of the subject by pushing from a vicinity of a proximal end of the support element. For some applications, support element 36 and electrodes 38 together are similar to conventional concentric needle electrodes, such as Medtronic, Inc. needle electrode model DCN50, or Oxford Instruments Plc. needle electrode models X53153, X53155, X53156, X53158, or X53159.

Each of electrodes 38 typically comprises a suitable conductive material, for example, a physiologically-acceptable material such as silver, iridium, platinum, a platinum iridium alloy, titanium, nitinol, or a nickel-chrome alloy. For some applications, each of the electrodes has a surface area of between about 1 and about 8 $mm^2$, such as about 2.653 or about 6.123 $mm^2$. For some applications, electrodes 38 are recessed within support element 36, while for other applications the electrodes are flush with the surface of the support element, or protrude therefrom. Electrodes 38 are insulated from one another with a physiologically-acceptable material such as polyethylene, polyurethane, or a co-polymer of either of these. For some applications, the electrodes are spiral in shape, for better contact, and may have a hook shaped distal end for hooking into or near the SPG. Alternatively or additionally, the electrodes may comprise simple wire electrodes, spring-loaded "crocodile" electrodes, or adhesive probes, as appropriate. For some applications, the electrodes are coated with a biocompatible material configured to enhance the surface area of the electrodes, thereby increasing the capacitance and reducing the resistance of the electrodes. For example, the material may comprise a platinum/iridium alloy, and/or may be applied with a sputtering process, such as commercially available from Johnson Matthey Plc, Advanced Metals Technology division (London, UK).

Optionally, support element 36 comprises one or more marks (not shown) that indicate the depth of insertion of stimulator 30 into greater palatine canal 54. Alternatively or additionally, for some applications support element 36 comprises a stopper (not shown) in a vicinity of the marks, that mechanically prevents insertion of the support element into the canal beyond a certain depth.

Reference is made to FIGS. 3A-B, 4A-B, and 5A-D, which are schematic illustrations of several configurations of stimulator 30, in accordance with respective embodiments of the present invention. In these embodiments, stimulator 30 comprises a circuit module 41, which comprises circuitry 40 coupled to a printed circuit board. Circuit module 41 has a generally flat shape, typically with a thickness of less than about 2 mm, such as less than about 1.2 mm, e.g., about 1.05 mm. For some applications, one or more layers of coating are applied to circuit module 41, such as in order to provide a conforming, thin, smooth, watertight, biocompatible, and/or mechanically-protective surface. For example, a first, innermost coating may comprise an inert biocompatible polymer, such as Parylene C, having a thickness of between about 10 and about 15 microns. A second watertight mineral-based sealant, such as $Al_2O_3$, $SiO_2$, or $Si_2N_3$, may be applied over the innermost coating by sputtering. The thickness of the watertight sealant is typically between about 1 and about 2 microns. A third, outermost coating of an inert biocompatible polymer, such as Parylene C, having a thickness of between about 10 and about 15 microns, may be applied over the watertight sealant.

Figure 3A:
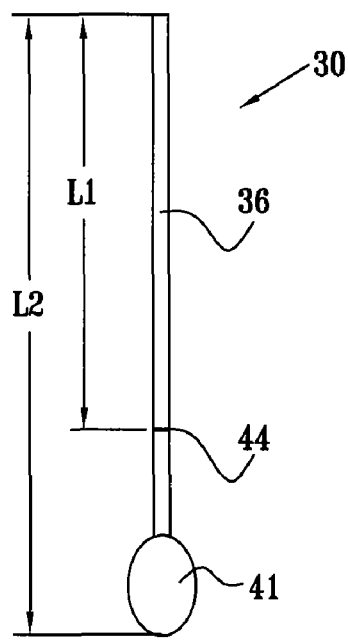
FIGS. 3A and 3B are schematic illustrations of a laterally displaced configuration of a stimulator of the system of FIG. 1, in accordance with an embodiment of the present invention.
Figure 3B:
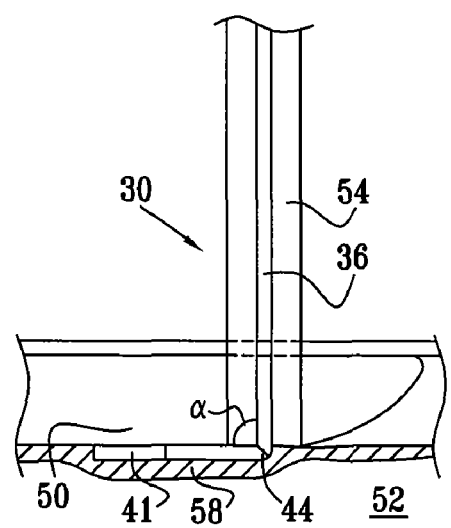

FIGS. 3A and 3B are schematic illustrations of a laterally displaced configuration of stimulator 30, in accordance with an embodiment of the present invention. FIG. 3A shows stimulator 30 in an unfolded position. Circuit module 41 has a generally flat shape, and may be generally elliptical, as shown in FIG. 3A, or may have another shape, such as rectangular. Prior to insertion in greater palatine canal 54, support element 36 is folded at a fold 44 at an angle α approximately equal to the angle between greater palatine canal 54 and hard palate 50 in a vicinity of foramen 42. During an implantation procedure, (a) a submucosal surface on the hard palate is prepared, such as by raising a mucosal flap, by creating a mucosal opening using a retractor, and/or by preparing a submucosal pocket using a tool which has generally the same shape and dimensions as circuit module 41, (b) support element 36 is inserted into greater palatine canal 54, (c) circuit module 41 is placed against the exposed lower surface of hard palate 50, and (d) mucosa 58 is closed over circuit module 41 and the portion of support element that protrudes from greater palatine canal 54. For implantation procedures during which a mucosal flap is raised, an approximately 3 cm incision is typically required to raise the mucosal flap. For some applications, the circuit module is coupled to the hard palate, such as by using at least one nail or screw (coupling not shown). Typically, the distal portion of support element 36 beyond fold 44 has a length L1 of between about 26 and about 30 mm, e.g., about 28 mm, and the entire stimulator 30 in an unfolded position, including circuit module 41, has a length L2 of between about 40 and about 44 mm, e.g., about 42 mm.

Figure 4A:
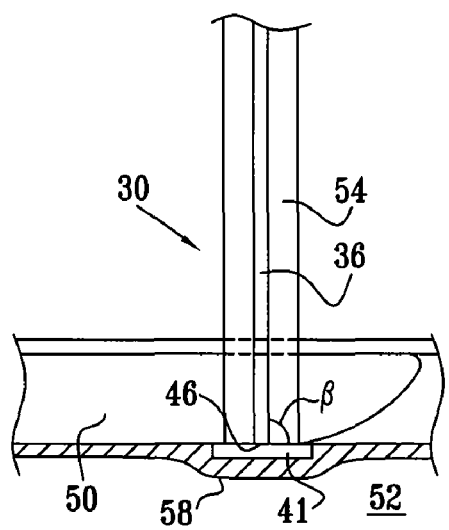
FIGS. 4A and 4B are schematic illustrations of out-of-plane configurations of the stimulator of the system of FIG. 1, in accordance with respective embodiments of the present invention.
Figure 4B:
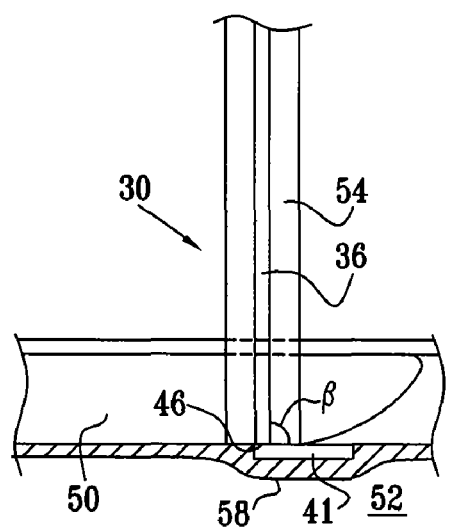

FIGS. 4A and 4B are schematic illustrations of out-of-plane configurations of stimulator 30, in accordance with respective embodiments of the present invention. In these configurations, a proximal end 46 of support element 36 is coupled directly to circuit module 41, such that an angle β between support element 36 and the surface of circuit module 41 is approximately equal to the angle between greater palatine canal 54 and hard palate 50 in a vicinity of foramen 42. As in the configuration shown in FIGS. 3A and 3B, circuit module 41 has a generally flat shape, and may be generally elliptical, or may have another shape, such as rectangular. In the configuration shown in FIG. 4A, proximal end 46 of support element 36 is coupled to circuit module 41 in a vicinity of a center of the surface of the circuit module. For some applications, the circuit module is coupled to the support element such that the longer axis or side of the circuit module is oriented in an anterior-posterior direction. Alternatively, the longer axis or side of the circuit module is oriented in a left-right direction, or in another direction. Typically, support element 36 has a length of between about 26 and about 30 mm, e.g., about 28 mm.

In the configuration shown in FIG. 4B, proximal end 46 is coupled to circuit module in a vicinity of an edge of the surface of the circuit module. The support element may be coupled to any point on the edge, e.g., in a vicinity of an end of a major axis or a minor axis of the circuit module. For some applications, proximal end 46 of support element 36 is coupled to circuit module 41 at a location between the center of the circuit module and the edge of the circuit module. For some applications, the circuit module is coupled to the support element such that the circuit module extends in an anterior direction, in a posterior direction, towards the center of the mouth, or towards the maxillary bone. For example, when the circuit module extends in a posterior direction or towards the center of the mouth, the circuit module is less likely to interfere with branches of the greater palatine nerve or greater palatine artery that extend in an anterior direction from greater palatine foramen 42. For some applications, circuit module 41 is generally kidney-shaped.

During an implantation procedure, (a) a submucosal surface on the hard palate is prepared, such as by raising a mucosal flap, by creating a mucosal opening using a retractor, and/or by preparing a submucosal pocket using a tool which has generally the same shape and dimensions as circuit module 41, (b) support element 36 is inserted into greater palatine canal 54, (c) circuit module 41 is placed against the exposed lower surface of hard palate 50, and (d) mucosa 58 is closed over circuit module 41. For implantation procedures during which a mucosal flap is raised, an approximately 7 mm incision is typically required to raise the mucosal flap. For some applications, the circuit module is coupled to the hard palate, such as by using at least one nail or screw (coupling not shown).

Figure 5A:
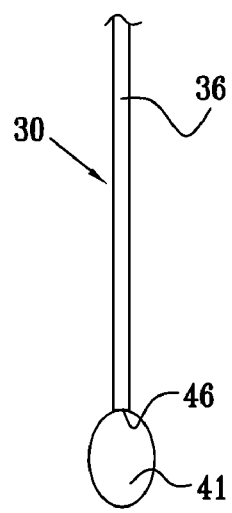
FIGS. 5A-D are schematic illustrations of a longitudinally-oriented configuration of the stimulator of the system of FIG. 1, in accordance with an embodiment of the present invention.
Figure 5B:
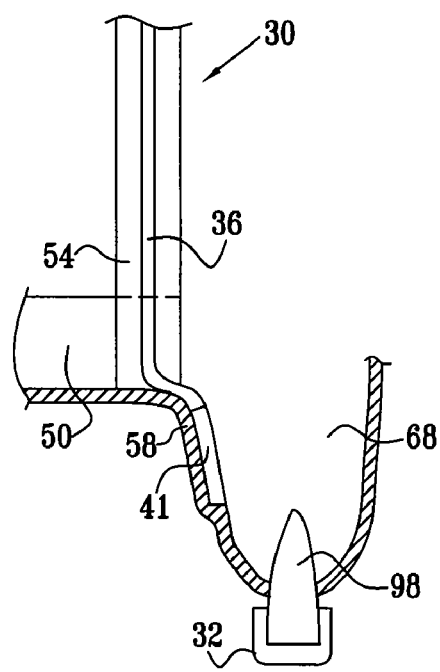
Figure 5C:
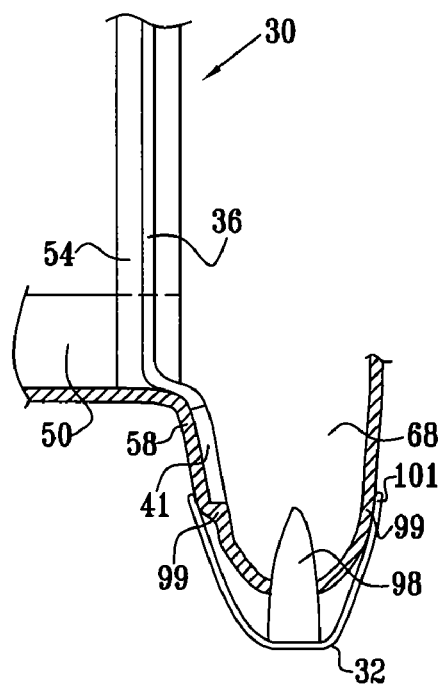
Figure 5D:
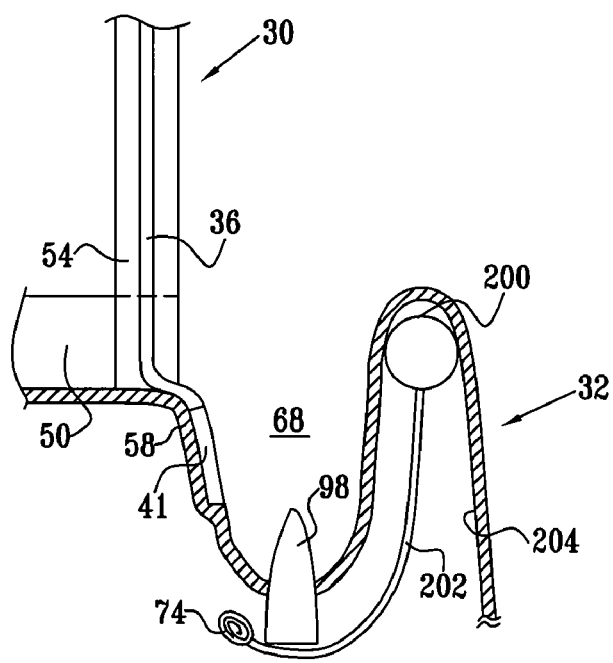

FIGS. 5A-D are schematic illustrations of a longitudinally-oriented configuration of stimulator 30, in accordance with an embodiment of the present invention. In this configuration, a proximal end 46 of support element 36 is coupled to circuit module 41. Circuit module 41 has a generally flat shape, and may be generally elliptical, as shown in FIG. 5A, or may have another shape, such as rectangular. As shown in FIGS. 5B-D, a proximal portion 48 of support element 36 which protrudes from greater palatine canal 54 is sufficiently flexible to follow the contour of the palate and alveolar process.

During an implantation procedure, (a) a submucosal surface on the hard palate is prepared, such as by raising a mucosal flap, by creating a mucosal opening using a retractor, and/or by preparing a submucosal pocket using a tool which has generally the same shape and dimensions as circuit module 41, (b) support element 36 is inserted into greater palatine canal 54, (c) circuit module 41 is placed against an alveolar process 68 of the maxilla, and (d) mucosa 58 is closed over circuit module 41. For implantation procedures during which a mucosal flap is raised, an approximately 5 mm incision is typically required to raise the mucosal flap. For some applications, the circuit module is coupled to the alveolar process, such as by using at least one nail or screw (coupling not shown).

Reference is made to FIGS. 6A-D, which are schematic illustrations of variable-length support elements 36, in accordance with respective embodiments of the present invention. In these embodiments, the length of support element 36 is adjustable during the implantation procedure, in order to accommodate differing lengths of greater palatine canal 54. It is noted that the variation in the length of the greater palatine canal in adults is generally less than +/−2 mm, so the length of support elements 36 in these embodiment need only vary by a relatively small percentage.

Figure 6A:
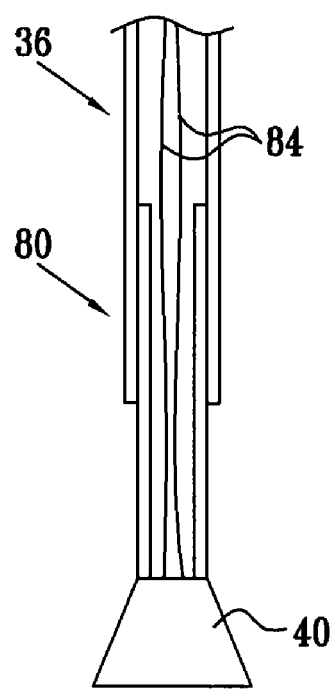
FIGS. 6A-D are schematic illustrations of variable-length support elements of the system of FIG. 1, in accordance with respective embodiments of the present invention.

In the configuration shown in FIG. 6A, support element 36 is configured to allow telescopic coupling of a portion 80 of the support element. Electrode leads 84 pass through support element 36, including portion 80. The leads have sufficient slack so as to not interfere with the expansion and contraction of telescopic portion 80.

Figure 6B:
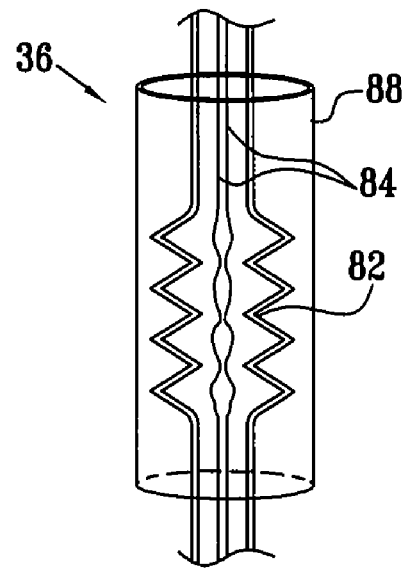

In the configuration shown in FIG. 6B, a portion of support element 36 is shaped so as to define one or more accordion pleats 82. Accordion pleats 82 are typically biased such that they are generally extended when in a relaxed position. Electrode leads 84 pass through support element 36, including the accordion portion. The leads have sufficient slack so as to not interfere with the expansion and contraction of accordion pleats 82. For some applications, support element 36 comprises a sleeve 88, which surrounds accordion pleats 82. The sleeve typically has a length no greater than the length of support element 36 when the support element is in its most contracted position, i.e., the sleeve surrounds only a portion of the non-accordion-pleated portion of the electrode leads. Such a length allows the total length of the support element to vary without being constrained by the length of the sleeve. Sleeve 88 typically comprises a flexible, biocompatible material, such as silicone. Sleeve 88 typically has a length less than 28 mm, e.g., less than 26 mm. Alternatively, for some applications, electrode leads 84 are accordion-pleated, in which case the electrode leads serve as support element 36.

Figure 6C:
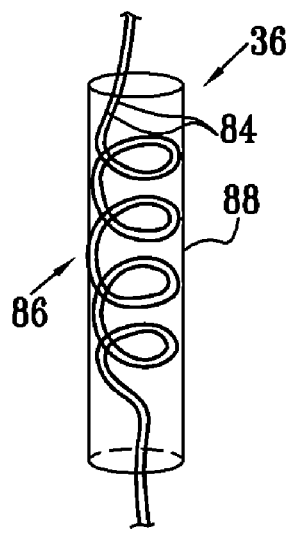

In the configuration shown in FIG. 6C, electrode leads 84 are helically wound, so as to form a spring 86. The spring is typically biased so as to have an expanded resting position. For some applications, support element 36 comprises sleeve 88, which surrounds spring 86. The sleeve typically has a length no greater than the length of support element 36 when the support element is in its most contracted position, i.e., the sleeve surrounds only a portion of the non-helically-wound portion of the electrode leads. Such a length allows the total length of the support element to vary without being constrained by the length of the sleeve.

Figure 6D:
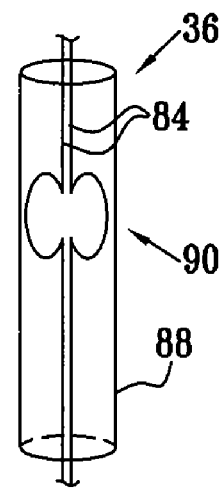

In the configuration in FIG. 6D, electrode leads 84 are shaped to as to define at least one omega-shaped portion 90. Portion 90 is typically biased so as to have extended resting positions. For some applications, support element 36 comprises sleeve 88, as described above with reference to FIGS. 6B and 6C.

Reference is made to FIGS. 7A-B, which are schematic illustration of oral element 32, in accordance with respective embodiments of the present invention. Oral element 32 is adapted to be placed in oral cavity 52 in a vicinity of implanted circuitry 40 of stimulator 30, e.g., in a vicinity of or in contact with the roof of the oral cavity. Oral element 32 typically comprises a power source 72, such as a rechargeable or disposable battery, circuitry 73, and at least one wireless coupling element 74. Depending on the specific application, wireless coupling element 74 transmits energy and/or data to circuitry 40, as described hereinbelow. For some applications, wireless coupling element 74 comprises a relatively large coil or a plurality of smaller coils, which may increase the likelihood that at least some portion of the generated magnetic field achieves good wireless coupling with implanted circuitry 40 of stimulator 30, even if oral element 32 is not precisely positioned or aligned with respect to stimulator 30, or if oral element 32 moves slightly after it has been placed against the roof of the oral cavity. For some applications in which wireless coupling element 74 comprises a plurality of coils, the coils are oriented with respect to one another such that the respective axes of the coils are not parallel with one another. For example, the coils may be oriented such that two or three of the axes are approximately orthogonal with one another.

In the embodiment shown in FIG. 7A, oral element 32 is adapted to be temporarily placed in oral cavity 52, without mechanically coupling the oral element to a surface of the oral cavity. For some applications, oral element 32 is coupled to an oral appliance, as described hereinbelow with reference to FIG. 8. In the embodiment shown in FIG. 7B, oral element 32 is adapted to be fixed to the roof of oral cavity 52, such as by using one or more screws 70, nails, or other surgical fastening devices.

FIG. 8 is a schematic illustration of oral element 32 coupled to an oral appliance 92, in accordance with an embodiment of the present invention. Oral appliance 92, which is typically shaped generally similarly to an orthodontic retainer, is configured to hold the oral element in a vicinity of or in contact with the roof of the oral cavity in a vicinity of implanted circuitry 40 of stimulator 30. The use of oral appliance 92, rather than mechanical coupling of oral element 32 to the roof of the oral cavity, generally reduces the likelihood of contamination. For some applications, oral appliance 92 is generally soft or semi-flexible, while for other applications, the oral appliance is generally rigid.

For some applications, oral element 32 does not comprise power source 72. Instead, power is provided by a power source located outside of the oral cavity. For example, the oral appliance may be coupled by a cable to an external driver comprising a power source. For some applications, the driver is coupled to a headset or necklace worn by the subject. The driver or a separate external control unit, instead of oral element 32, comprises all or a portion of circuitry 73. For some applications, the driver is coupled to external control unit 34, while for other applications, the driver comprises external control unit 34. Alternatively, oral element 32 is wirelessly coupled to external control unit 34, which may or may not be coupled to the external driver.

Reference is again made to FIGS. 5B-D. In the embodiment of the present invention shown in FIG. 5B, oral element 32 is configured to be coupled to a molar 98 or other tooth of the subject. For example, the oral element may comprise a clip or adhesive. Typically, the oral element is configured to be removably coupled to the tooth. For example, the oral element may be coupled to the tooth only during applications of stimulation by stimulator 30, and removed between applications of stimulation.

In the embodiment shown in FIG. 5C, oral element 32 is configured to be coupled to gingiva 99 covering alveolar process 68, and, optionally, to one or more teeth. For some applications, the oral element 32 is coupled to gingival 99 using a clamp 101. Alternatively or additionally, the oral element is adapted to be held in place by the subject biting down on the element.

In the embodiment shown in FIG. 5D, oral element 32 comprises a capsule 200, which, for some applications, comprises power source 72 and circuitry 73. Oral element 32 further comprises an elongated connecting element 202, which couples capsule 200 to wireless coupling element 74. Capsule 200 is configured to be placed and held between alveolar process 68 and the inner surface of a cheek 204. For some applications, capsule 200 is generally cylindrical, similar in shape and size to a conventional dental cotton roll. Optionally, the capsule comprises a soft coating. Oral element 32 is configured such that wireless coupling element 74 is positioned on the lingual side of the teeth. For some applications, connecting element 202 passes over the occlusal surface of one or more teeth, as shown in FIG. 5D, while for other applications, connecting element 202 passes around the distal surface of the most distal molar (configuration not shown). Alternatively, connecting element 202 serves as wireless coupling element 74.

For some applications, capsule 200 does not comprise power source 72. Instead, power is provided by a power source located outside of the oral cavity. For example, the capsule may be coupled by a cable to an external driver comprising a power source. For some applications, the driver is coupled to a headset or necklace worn by the subject. The driver or a separate external control unit, instead of capsule 200, comprises all or a portion of circuitry 73. For some applications, the driver is coupled to external control unit 34, while for other applications, the driver comprises external control unit 34.

In an embodiment of the present invention, system 20 comprises a nasal element instead of or in addition to oral element 32 (configuration not shown). The nasal element is adapted to be inserted into a nostril of the subject, e.g., into the nasal vestibule. The nasal element comprises at least one wireless coupling element 74 that is wirelessly coupled to transmit/receiver 40 of stimulator 30, for transmitting/receiving power and/or data to/from the stimulator. In this embodiment, circuitry 40 of stimulator 30 is not necessarily positioned at the proximal end of the stimulator.

For some applications, circuitry 40 of stimulator 30 comprises a wireless coupling element. Wireless coupling element 74 of oral element 32 is adapted to wirelessly transmit energy and/or data to the wireless coupling element of circuitry 40, and/or to wirelessly receive data form the wireless coupling element of circuitry 40. For these applications, each of the wireless coupling elements typically comprises at least one coil. For some applications, the wireless coupling elements are wirelessly coupled to one another using induction, such as when the wireless coupling elements are positioned in close proximity to one another. Alternatively, the wireless coupling elements are wirelessly coupled to one another using RF energy, such as when the wireless coupling elements are positioned at a greater distance from each other. Further alternatively, the wireless coupling elements are wirelessly coupled to one another using another form of energy, such as ultrasound energy, in which case the wireless coupling elements comprises ultrasound transducers, e.g., piezoelectric transducers. "Transducer element," as used in the present application including the claims, means an element adapted to wirelessly transmit and/or receive energy and/or data, including a coil, a piezoelectric transducer, and other wireless transducers known in the art.

In an embodiment of the present invention, oral element 32 does not comprise wireless coupling element 74. Instead, power source 72 of the oral element is coupled to circuitry 40 using a wire that passes through mucosa 58. The techniques of this embodiment are generally more energy-efficient than wireless energy/data transfer techniques. As a result, the battery of power source 72 of oral element 32 may need to be replaced or recharged less frequently, or not at all. For some applications, oral element 32 is adapted to be implanted in a tooth of the subject. For some applications, the implanted oral element comprises a wireless communication element for external wireless communication, such as of data. For some applications, power source 72 comprises a rechargeable or a replaceable battery.

Reference is made to FIG. 9, which is a schematic illustration of a contact-based energy transmission configuration of stimulation system 20, in accordance with an embodiment of the present invention. In this embodiment, a proximal end of support element 36 of stimulator 30 comprises a contact 94 that protrudes slightly from mucosa 58. Oral element 32 comprises a contact 96, which is brought into physical contact with contact 94 for transmitting power and/or data to/from circuitry 40. Contact 94 of stimulator 30 is typically in sealed contact with mucosa 58, in a similar manner to pacemaker leads. For some applications, contact 94 is typically semi-spherical in shape, as shown in FIG. 9. Alternatively, contact 94 is generally flat or concave in shape. The use of the contact-based techniques of this embodiment does not require alignment of oral element 32 with circuitry 40. In addition, the contact-based techniques of this embodiment result in a uniform, predictable transfer of energy, and are generally more energy-efficient than wireless energy/data transfer techniques. As a result, the battery of power source 72 of oral element 32 may need to be replaced or recharged less frequently, or not at all.

FIG. 10 is a schematic illustration of a configuration of contact 94, in accordance with an embodiment of the present invention. In this embodiment, contact 94 comprises positive and negative terminals 95 and 96, each of which is coupled to a respective lead 84. For some applications, support element 36, at a portion thereof which passes through mucosa 58, comprises a matrix 97, which is adapted to promote mucosal tissue growth therein. The growth of mucosal tissue in the matrix generally reduces the likelihood of infection, and helps hold contact 94 in place. For some applications, contact 94 and/or matrix 97 is coated with an antiseptic substance, such as an antibacterial substance, to reduce the likelihood of infection passing from the oral cavity through the mucosa.

Reference is made to FIG. 11A, which is a schematic illustration of energy and data transmission paths between components of system 20, in accordance with an embodiment of the present invention. Typically, wireless coupling element 74 of oral element 32 is adapted to wirelessly transmit energy to circuitry 40 of stimulator 30, for powering the stimulator, as symbolically indicated by an arrow 100. The close proximity of the wireless coupling elements of oral element 32 and stimulator 30 generally allows the use of relatively low energy levels and/or a small receiving element in circuitry 40, e.g., a small coil or piezoelectric transducer.

In an embodiment of the present invention, the energy transmitted to circuitry 40 of stimulator 30 does not include the stimulation waveform to be applied using electrodes 38. Instead, energy is typically transferred using a continuous wave (i.e., electromagnetic energy of constant amplitude and frequency). Circuitry 40 of stimulator 30 is configured to generate the stimulation waveform applied by electrodes 38. Alternatively, the energy is transferred using a quasi-continuous wave, which encodes data, which data is used by circuitry to generate the stimulation waveform applied by electrodes 38. The techniques of this embodiment may be employed, for example, with the configurations of stimulation system 20 described hereinabove with reference to FIGS. 1 and/or 8, and/or hereinbelow with reference to FIGS. 12-14 and/or 15. The transfer of energy only, in accordance with this embodiment, generally allows complete control of the waveform delivered by electrodes 38, because the generation of the waveform is independent of the wireless coupling of oral element 32 and circuitry 40 of stimulator 30. Furthermore, for some applications, circuitry 40 generates a bipolar waveform, which typically reduces the total accumulated charge in the tissue, thus improving safety and electrode life span.

For some applications, wireless coupling element 74 of oral element 32 is additionally configured to transmit and/or receive data to/from circuitry 40 of stimulator 30, as indicated by an arrow 102. Such data typically includes stimulation control signals, parameters, and/or feedback information. Such data is typically transmitted only periodically, rather than constantly during stimulation. Circuitry 40 of stimulator 30 configures at least a portion of the stimulation parameters based on the received information. For these applications, circuitry 40 of stimulator 30 is configured to generate the stimulation waveform applied by electrodes 38, based on the configured parameters.

For some applications, wireless coupling element 74 of oral element 32 (either the same wireless coupling element used for transmitting and receiving data to and from circuitry 40 of stimulator 30, or a separate wireless coupling element) is adapted to wirelessly relay the data to and receive data from external control unit 34 (as indicated by an arrow 104), which also comprises a wireless coupling element 106. Typically, but not necessarily, substantive processing and generation of the data is performed exclusively by external control unit 34, rather than by oral element 32. For some applications, wireless coupling element 74 combines the data and the energy transmitted to circuitry 40 of stimulator 30 into a single signal, such as by modulating the data onto the carrier frequency of the transmitted energy, in which case circuitry 40 demodulates the received signal to obtain the data. Alternatively, wireless coupling element 74 transmits the data and the energy in separate signals. Alternatively, for some applications, circuitry 40 of stimulator 30 is configured to transmit and/or receive all or a portion of the data directly to/from external control unit 34 (as indicated by an arrow 108), bypassing oral element 32, such as by using a VHF signal.

For some applications in which the energy is transferred using a continuous wave, the energy is transferred from outside the body of the subject, e.g., from a vicinity of the cheek or ear of the subject, rather than from oral element 32. This is possible because the continuous wave generally has low peak power levels. For these applications, system 20 typically does not comprise oral element 32.

In an embodiment of the present invention, circuitry 73 of oral element 32 generates the stimulation waveform, and wirelessly transmits the waveform to circuitry 40 of stimulator 30. For these applications, circuitry 40 of stimulator 30 is generally passive, and simply relays the received waveform to electrodes 38 with minimal or no processing. Circuitry 40 typically comprises a simple circuit, including one or more rectifiers and capacitors. The techniques of this embodiment may be employed, for example, with the configurations of stimulation system 20 described hereinabove with reference to FIGS. 1, 8, and/or 9.

For some applications, system 20 is configured to perform a calibration procedure in which the absolute energy level of the applied waveform is determined, and adjusted appropriately to achieve a desired stimulation level. Such calibration compensates for the patient-to-patient variability in energy transfer, caused, for example, by differences in placement and/or orientation of oral element 32 or circuitry 40 of stimulator 40, and/or inter-patient anatomical differences, e.g., thickness of the mucosa.

Reference is made to FIG. 11B, which is a schematic illustration of energy and data transmission paths between components of system 20, in accordance with an embodiment of the present invention. Except as described hereinbelow, this embodiment is similar to the embodiment described hereinabove with reference to FIG. 11A. In this embodiment, system 20 additionally comprises an external driver 110, which comprises power source 72 and circuitry 73. Oral element 32 comprises wireless coupling element 74, but typically does not comprise power source 72 or circuitry 73 (the oral element and/or the wireless coupling element may comprise minimal circuitry, such as one or more rectifiers or capacitors). Oral element 32 is electrically coupled to external driver 110 by an elongated flexible coupling element 112, which comprises one or more wires. Driver 110 is typically adapted to be physically coupled to a body of the subject, such as by being coupled to headset or a necklace.

Driver 110 typically comprises a wireless coupling element 114, which the driver uses to wirelessly relay data to and receive data from external control unit 34 (as indicated by an arrow 116). For example, the data may be transmitted using the Bluetooth protocol or another wireless communication protocol, or using an infrared signal. Alternatively, driver 110 is coupled to external control unit 34 by one or more wires (configuration not shown).

Reference is made to FIG. 12, which is a schematic illustration of a neural stimulation system 120, in accordance with an embodiment of the present invention. Except as noted hereinbelow, elements of system 120 are the same as corresponding elements of system 20 having the same reference numerals. System 120 comprises implantable neural stimulator 30 and external control unit 34. Stimulator 30 comprises elongated support element 36, one or more electrodes 38 fixed to the support element in the vicinity of the distal end thereof, and an implantable submucosal antenna 122 coupled to the support element in a vicinity of the proximal end thereof. Submucosal antenna 122 is adapted to be implanted in the roof of oral cavity 52 between oral mucosa 58 and a palate, e.g., hard palate 50 and/or a soft palate 134, and to generally conform to the shape of the palate.

Figure 13:
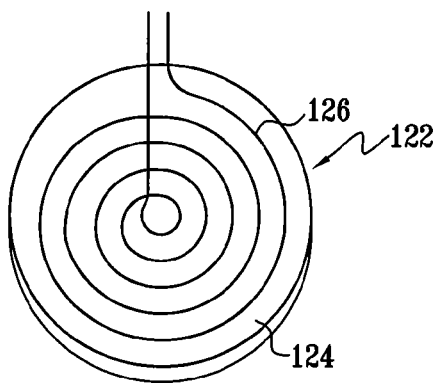
FIG. 13 is a schematic illustration of an implantable submucosal antenna of the system of FIG. 12, in accordance with an embodiment of the present invention.

FIG. 13 is a schematic illustration of implantable submucosal antenna 122, in accordance with an embodiment of the present invention. Submucosal antenna 122 comprises a thin, flexible sheet 124, which comprises at least one coil 126. Sheet 124 comprises a flexible biocompatible material, such as silicone.

Figure 14A:
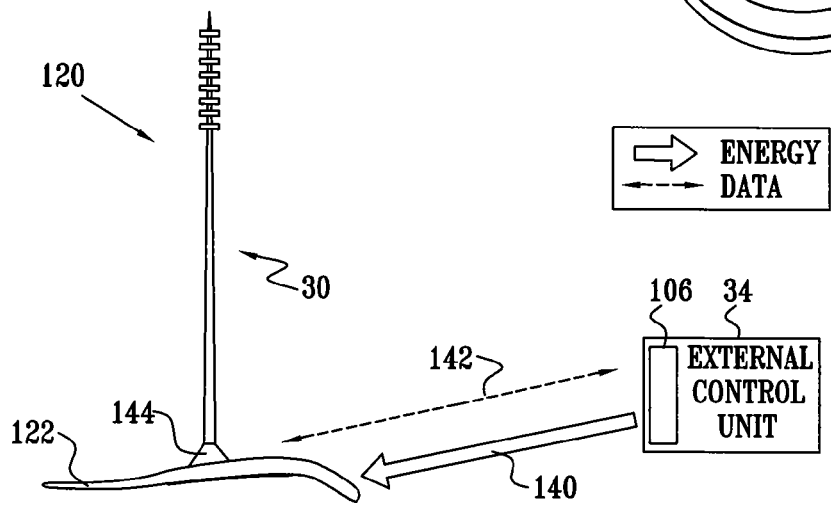
FIGS. 14A-B are schematic illustrations of energy and data transmission paths between components of the system of FIG. 12, in accordance with respective embodiments of the present invention.

Reference is made to FIG. 14A, which is a schematic illustration of energy and data transmission paths between components of system 120, in accordance with an embodiment of the present invention. System 120 typically lacks oral element 32 of system 20. Instead, external control 34 unit is adapted to transmit power, typically using RF energy, directly to submucosal antenna 122, for powering stimulator 30, as indicated by an arrow 140, and to transmit and/or receive data directly to/from the submucosal antenna, as indicated by an arrow 142. Such data typically includes stimulation control signals, parameters, and/or feedback information. Such data is typically transmitted only periodically, rather than constantly during stimulation. Circuitry 40 of stimulator 30 is configured to generate the stimulation waveform applied by electrodes 38, based on the configured parameters.

For some applications, wireless coupling element 106 combines the data and the energy into a single signal, such as by modulating the data onto the carrier frequency of the transmitted energy, in which case submucosal antenna 122 demodulates the received signal to obtain the data. Alternatively, wireless coupling element 106 transmits the data and the energy in separate signals. Alternatively, for some applications, stimulator 30 additionally comprises a wireless coupling element 144, to/from which external control unit 34 transmits and/or receives data, such as by using a VHF signal. Typically, external control unit 34 is adapted to be placed in a vicinity of a head of the subject, such as in a vicinity of an ear of the subject. For some applications, external control unit 34 is adapted to be coupled to the ear. For example, the control unit may comprise or be integrated into a wired or wireless headset, such as a cellular phone headset.

Figure 14B:
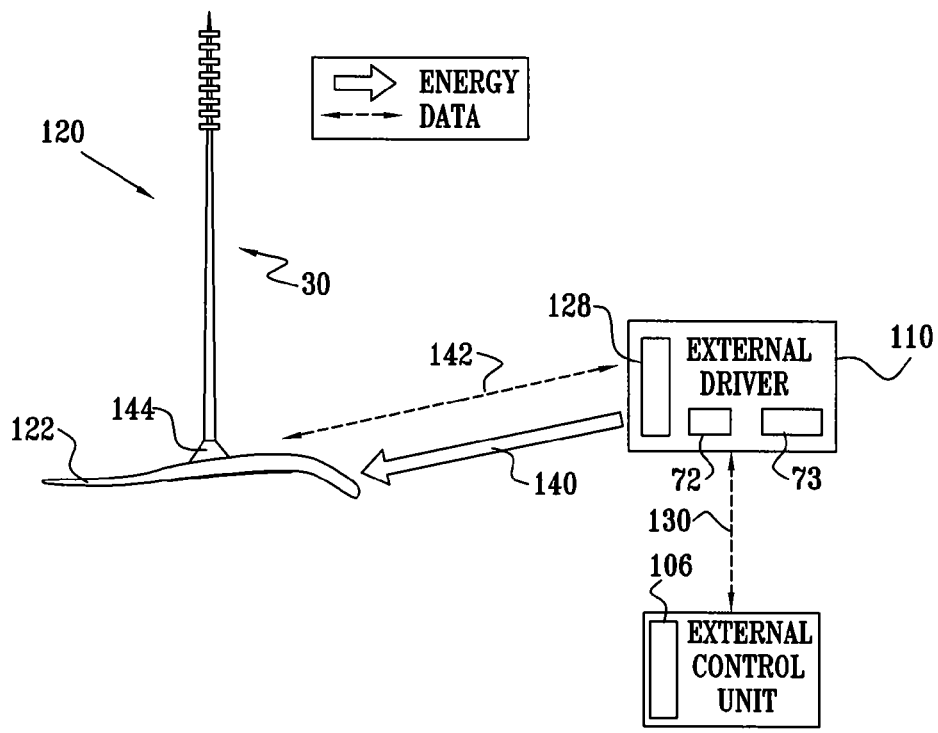

Reference is made to FIG. 14B, which is a schematic illustration of energy and data transmission paths between components of system 120, in accordance with an embodiment of the present invention. Except as described hereinbelow, this embodiment is similar to the embodiment described hereinabove with reference to FIG. 14A. In this embodiment, system 120 additionally comprises external driver 110, which comprises power source 72, circuitry 73, and at least one wireless coupling element 128. Driver 110 is typically adapted to be worn by the subject, such as by being coupled to headset or a necklace. Driver 110 is adapted to use wireless coupling element 128 to transmit power, typically using RF energy, directly to submucosal antenna 122, for powering stimulator 30, as indicated by an arrow 140, and to transmit and/or receive data directly to/from the submucosal antenna, as indicated by an arrow 142.

Driver 110 typically uses wireless coupling element 128, or a separate wireless coupling element (not shown), to wirelessly relay data to and receive data from external control unit 34 (as indicated by an arrow 130). For example, the data may be transmitted using the Bluetooth protocol or another wireless communication protocol, or using an infrared signal. Alternatively, driver 110 is coupled to external control unit 34 by one or more wires (configuration not shown).

Figure 15:
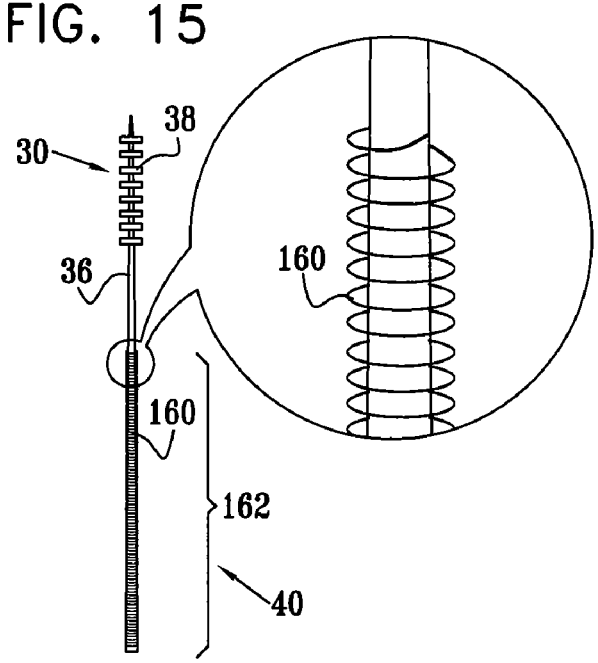
FIG. 15 is a schematic illustration of a configuration of the stimulator of the stimulation system of FIGS. 12-14, in accordance with an embodiment of the present invention.

Reference is made to FIG. 15, which is a schematic illustration of a configuration of stimulator 30 for use in stimulation system 120, described hereinabove with reference to FIGS. 12-14, in accordance with an embodiment of the present invention. In this embodiment, instead of submucosal antenna 122, system 120 comprises a coil antenna 160, at least a portion of which is coiled around at least a portion 162 of support element 36. Alternatively, coil antenna 160 is an integral part of portion 162. For some applications, coil antenna 160 comprises ferrite. For some applications, a sleeve is placed around all or a portion of coil antenna 160 and/or support element 36 (configuration not shown). Typically, the distal end of support element 36 comprises surgical punch 60, described hereinabove with reference to FIG. 1. For some applications, coil antenna 160 comprises a plurality of coils arranged in various orientations, which generally improves wireless coupling with wireless coupling element 106 of external control unit 34. For example, the plurality of coils may comprise two or three coils oriented approximately orthogonally to one another. In the configuration shown in FIG. 15, support element 36 and coil antenna 160 are typically adapted to be contained entirely within greater palatine canal 54.

Figure 16:
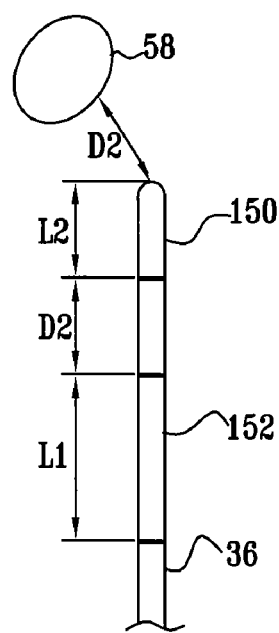
FIG. 16 is a schematic illustration of an electrode configuration, in accordance with an embodiment of the present invention.

Reference is made to FIG. 16, which is a schematic illustration of a configuration of electrodes 38, in accordance with an embodiment of the present invention. In this embodiment, electrodes 38 comprise at least one (e.g., exactly one) cathode 150, and at least one (e.g., exactly one) anode 152. Cathode 150 is typically located closer to a distal tip 154 of support element 36 than is anode 152. Typically, a length L1 of anode 152 is greater than a length L2 of cathode 150, such as at least 200% of length L2. A closest distance D1 between cathode 150 and anode 152 is typically greater than a closest distance D2 between any portion of cathode 150 and any portion of SPG 56.

In an embodiment of the present invention, a method for implanting stimulator 30 in greater palatine canal 54 comprises placing the stimulator in a bore of a needle having a sharp distal tip, passing the needle through mucosa 58 and greater palatine foramen 42, into canal 54, and withdrawing the needle, thereby leaving the stimulator implanted in the canal. Alternatively, the needle is first passed into canal 54, and stimulator 30 is subsequently introduced into the bore of the needle. The needle is typically passed through mucosa 58 without requiring a prior surgical incision in the mucosa, i.e., without requiring the use of a surgical knife or other tool. Alternatively, prior to insertion of the needle into the canal, a submucosal surface on the hard palate is prepared, such as by raising a mucosal flap, and/or by creating a mucosal opening using a retractor.

Figure 17A:
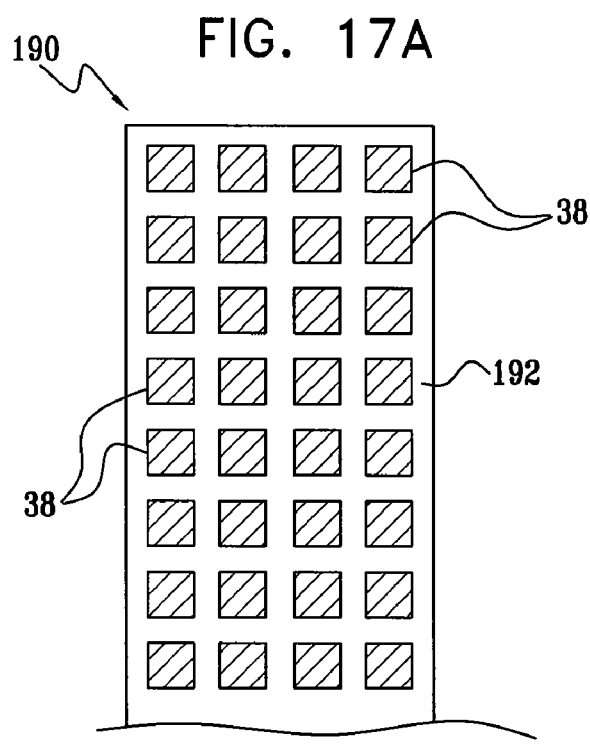
FIGS. 17A-C are schematic illustrations of an array of electrodes, in accordance with an embodiment of the present invention.
Figure 17B:
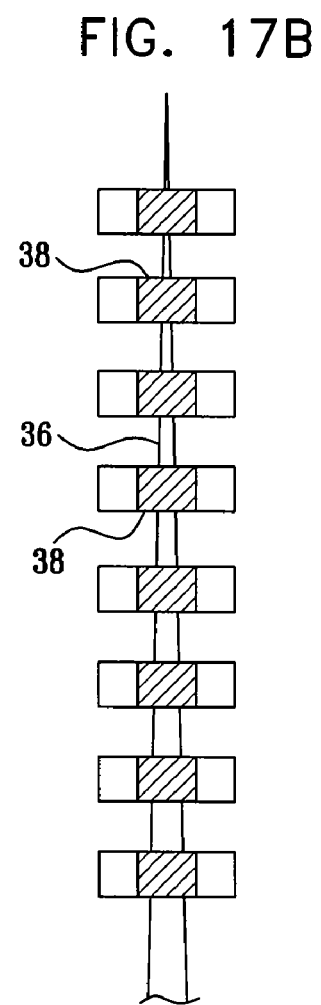
Figure 17C:
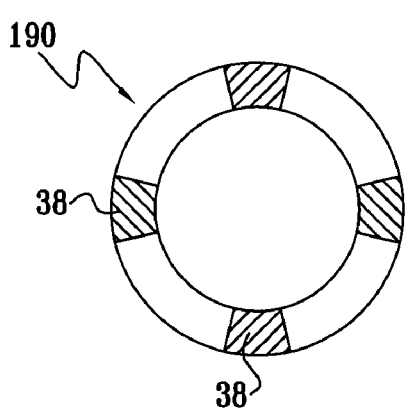

Reference is made to FIGS. 17A-C, which are schematic illustrations of an array 190 of electrodes 38, in accordance with an embodiment of the present invention. In this embodiment, stimulator 30 of system 20 or 120 comprises array 190, which typically comprises between about 8 and about 32 electrodes 38, such as about 32 electrodes. FIG. 17A shows array 190 in a flat, unrolled position. Typically, the array is organized in rows and columns, for example, between about 2 and about 8 rows, e.g., 8 rows, and between about 2 and about 4 columns, e.g., 4 columns. FIG. 17B shows array 190 encircling support element 36 (only a single column of electrodes 38 is visible in the figure). (For the sake of illustration, support element 36 is visible between electrodes 38 in FIG. 17B; in actual applications, a portion of the support element may be concealed by structural elements of array 190.) FIG. 17C is a cross-sectional top-view of one row of electrodes 38. For some applications, array 190 is fabricated on a flat substrate 192 (FIG. 17A), which is wrapped around support element 36 (FIG. 17B). For some applications, substrate 192 extends longitudinally along all or a portion of the length of support element 36, electrodes 38 are positioned in a distal region of the substrate, and circuitry of stimulator 30, such as circuitry 40, amplifier, and/or filters, is affixed to the substrate, e.g., in a proximal region of the substrate. For other applications, stimulator 30 does not comprise substrate 192, and electrodes 38 are coupled directly to, or are integral with, support element 36. It is noted that although stimulator 30 is generally shown in the figures as comprising array 150 of electrodes 38, this is for the sake of illustration only; embodiments described and shown herein may use the electrode configuration described hereinabove with reference to FIG. 16; electrode configurations described in U.S. patent application Ser. No. 10/783,113, such as with reference to FIG. 12, 13, or 14 thereof; electrode configurations described in the other patent applications incorporated by reference hereinbelow; or electrode configurations known in the art of neural stimulation.

In an embodiment of the present invention, stimulator 30 comprises a plurality of electrodes, at least a portion of which are adapted to be separately activatable. System 20 or 120 is adapted to use a calibration algorithm to activate, during a plurality of calibration periods, respective different sets of one or more of electrodes 38, in order to determine which set's activation causes a level of stimulation of the SPG closest to a desired level. For example, the desired level may be the maximum level that can be achieved for a given set of stimulation parameters. For some applications, the algorithm is alternatively or additionally used for setting a level of one or more stimulation parameters. System 20 or 120 typically uses the algorithm to determine the optimum set of electrodes after stimulator 30 has been implanted, so as to obviate the need to adjust the location of the stimulator after it has been implanted. Alternatively or additionally, the position of stimulator 30 is adjusted responsively to information derived using the algorithm. For some applications, during post-calibration (i.e., therapeutic) stimulation, the system activates different sets of electrodes at different times, such as in order to vary the level of stimulation applied to the SPG.

In an embodiment of the present invention, the level of stimulation of the SPG is determined by receiving feedback directly from the SPG, or from other neural tissue in a vicinity of the SPG, i.e., by using at least a portion of electrodes 38 to directly measure a level of stimulation of the SPG or the other neural tissue at or in a vicinity of the site(s) of the stimulation by the electrodes. For some applications, the at least a portion of electrodes 38 measure an electrical field of nervous tissue of the SPG or the other neural tissue induced by the electrical stimulation of the SPG. Typically, the signal generated by the sensed field is filtered to remove any artifacts in the signal generated by the stimulation applied by electrodes 38.

For some applications, the same set of one or more electrodes applies stimulation and measures the achieved stimulation of the SPG, by measuring the level of stimulation of the SPG or the other neural tissue. For other applications, a first set of one or more electrodes applies the stimulation, and a second set of one or more electrodes measures the achieved stimulation. Typically, the second set of electrodes is located in a vicinity of the first set of electrodes, and/or adjacent to the first set of electrodes in array 190.

Alternatively or additionally, for some applications, the level of stimulation of the SPG is determined by assessing an indirect physiological parameter of the subject related to the level of SPG stimulation, such as cerebral blood flow (CBF) and/or BBB permeability. For some applications, assessment techniques described hereinbelow are used. For some applications, a healthcare worker enters the values of the indirect physiological parameter into system 20, while for other applications, a device for measuring the indirect physiological parameters is coupled to system 20, and communicates the parameters to the system.

For some applications, system 20 is configured to select the desired set of electrodes 38. Alternatively or additionally, system 20 comprises an output unit, such as a display, which presents the results of the calibration algorithm to a healthcare worker, who selects the desired set of electrodes.

In an embodiment of the present invention, stimulator 30 is autonomically powered, such as by utilizing temperature differentials within the subject, e.g., using techniques described in the above-mentioned U.S. Pat. Nos. 6,470,212 to Weijand et al. and 6,640,137 to MacDonald, mutatis mutandis, or other techniques known in the art for generating energy from biological processes for powering an implanted medical device. For some applications, circuitry 40 of stimulator 30 does not comprise a wireless coupling element, or the wireless coupling element is used only for data transmission, rather than for wirelessly receiving energy. In the latter case, data is typically transmitted from and/or to external control unit 34.

In an embodiment of the present invention, electrodes 38 are located in a vicinity of a proximal end of support element 36, such that the electrodes apply electrical stimulation to greater palatine nerve 66 in a vicinity of the proximal opening of greater palatine foramen 42. For example, a closest distance between the electrodes and the proximal opening of the greater palatine foramen may be less than 10 mm, e.g., less than 5 mm. For some applications, upon implantation of stimulator 30, electrodes 38 are contained entirely within greater palatine canal 54, while for other applications, all or a portion of the electrodes are located submucosally outside of the canal and the foramen.

Although electrodes 38 have been described as being applied to an SPG of the subject, for some applications the electrodes are applied to another MTS of the subject, as defined hereinabove. For some of these applications, electrodes 38 are passed through the greater palatine canal to the MTS, while for other applications the electrodes are passed through only a portion of the greater palatine canal, or are advanced to the MTS by another route.

Figure 18:
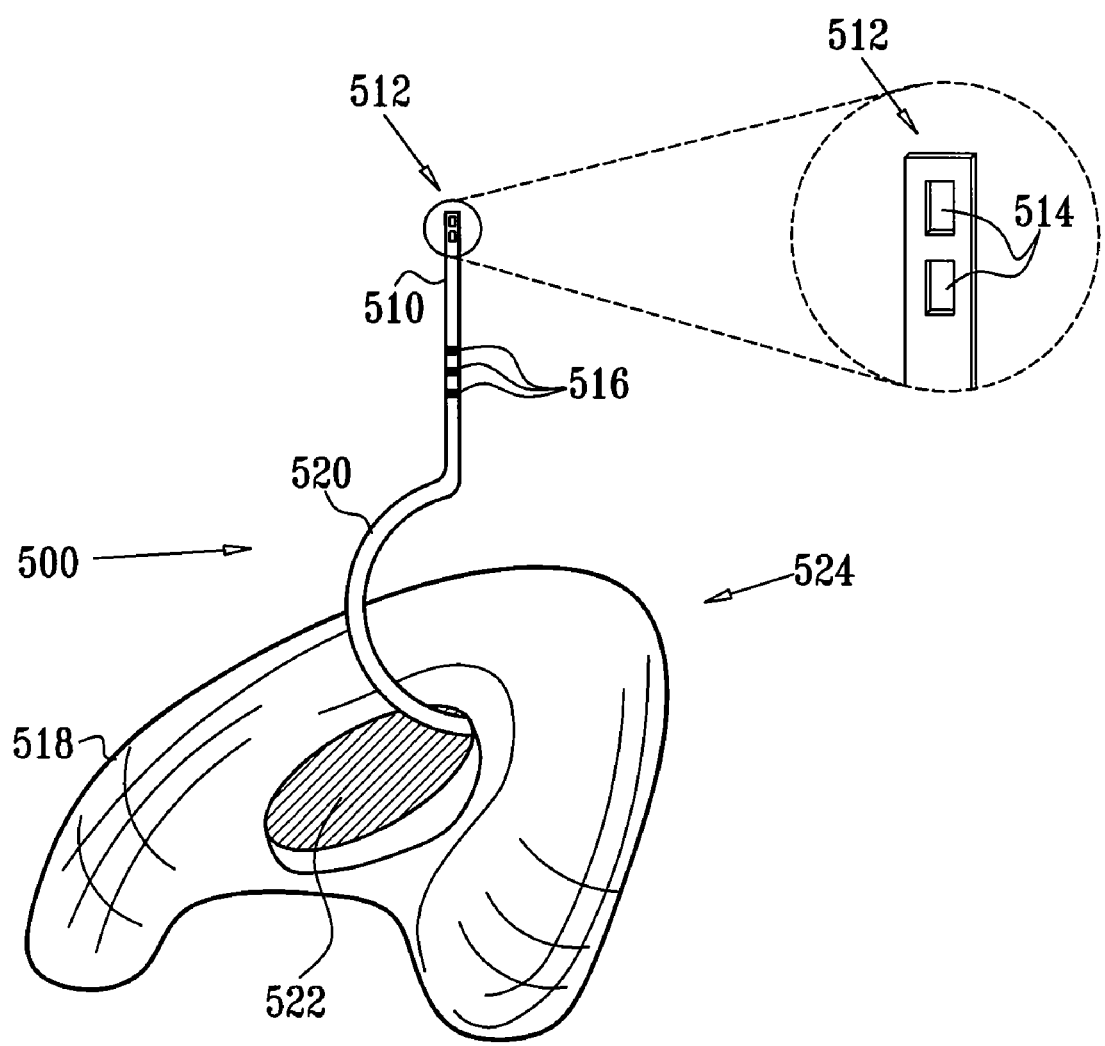
FIG. 18 is a schematic pictorial view of a stimulation system for stimulation of a modulation target site, in accordance with an embodiment of the present invention.

FIG. 18 a schematic pictorial view of a stimulation system 500, for stimulation of a sphenopalatine ganglion (SPG) system, as defined hereinabove, and/or at least one other appropriate "modulation target site" (MTS), as defined hereinabove, such as SPG 56, in accordance with an embodiment of the present invention. Stimulation system 500 comprises a support element 510, which typically, but not necessarily, is generally rigid (i.e., it generally keeps its original shape during a placement procedure). A distal end 512 of support element 510 comprises one or more electrodes 514. For some applications, electrodes 514 are recessed within support element 510, as shown in the figure, while for other applications the electrodes are flush with the surface of the support element, or protrude therefrom. Alternatively, the electrodes are configured as shown in FIGS. 13 and 14 of U.S. patent application Ser. No. 10/783,113.

Support element 510 is adapted to be inserted into a vicinity of an MTS or an SPG system of the subject, as defined hereinbelow, via a greater palatine canal in a roof of an oral cavity of the subject. Typically, support element 510 is substantially straight. Support element 510 typically comprises one or more marks 516 that indicate the point at which the support element has been sufficiently inserted into the greater palatine canal. Alternatively or additionally, support element 510 comprises a stopper (not shown) in a vicinity of marks 516, that mechanically prevents further insertion of the support element into the canal.

Stimulation system 500 further comprises a semi-flexible oral appliance 518, which is physically coupled to support element 510 by flexible leads 520. Oral appliance 518 comprises a neurostimulator 522, which is electrically coupled to electrodes 514 via leads 520. An upper surface 524 of oral appliance 518 is shaped to fit closely to the roof of the oral cavity, and is adapted to be coupled thereto. For example, oral appliance 518 may be shaped generally similarly to an orthodontic retainer. Neurostimulator 522 is typically battery-powered, and configurable to drive electrodes 514 to stimulate the MTS or SPG system. For some applications, the subject himself activates neurostimulator 522. Stimulation system 500 is typically adapted to remain in the oral cavity for between several hours and about two days.

In an embodiment of the present invention, a stimulation system for application to a subject comprises an elongated support element having a length of between about 1.8 cm and about 4 cm, such as a length of between about 1.8 cm and about 3 cm. The support element comprises one or more electrodes fixed thereto in a vicinity of a distal end thereof. The stimulation system further comprises a control unit, coupled to the support element in a vicinity of a proximal end thereof. The control unit typically comprises a battery, and is adapted to drive the electrodes to apply an electrical current to tissue of the subject, such as the SPG system and/or at least one MTS. The control unit typically configures the current to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes. (Together, the on and off periods define a duty cycle.) For example, the control unit may drive the electrodes to apply the current having on periods of between about 60 seconds and about 105 seconds, and off periods of between about 30 seconds and 90 seconds, e.g., on periods of about 90 seconds, and off periods of about 60 seconds.

For some applications, the support element is semi-rigid. For example, the support element and the electrodes together may be similar to conventional concentric needle electrodes, such as Medtronic, Inc. needle electrode model DCN50, or Oxford Instruments Plc. needle electrode models X53153, X53155, X53156, X53158, or X53159.

For some applications, the stimulation system comprises an oral appliance, coupled to the support element, and shaped so as to define a surface that fits closely to a roof of an oral cavity. For example, the oral appliance may be similar to oral appliance 518, described hereinabove with reference to FIG. 18. For some applications, the control unit has a volume, including the battery, of less than about 3 cm$^3$.

In an embodiment of the present invention, a stimulation system for application to a subject comprises an elongated support element having a length of between about 1.8 cm and about 4 cm, such as a length of between about 1.8 cm and about 3 cm. The support element comprises one or more electrodes fixed thereto in a vicinity of a distal end thereof, and a receiver, fixed to the support element in a vicinity of the proximal end thereof. The stimulation system further comprises a control unit, adapted to be coupled to the receiver. The control unit is adapted to drive the electrodes via the receiver to apply an electrical current to tissue of the subject, such as the SPG system and/or at least one MTS. The control unit typically configures the current to have a pulse frequency of between about 10 Hz and about 50 Hz, an amplitude of between about 0.2 V and about 10 V, a pulse width of between about 50 microseconds and about 5 milliseconds, and, in alternation, on periods of between about 1 second and about 2 minutes, and off periods of between about 1 second and about 2 minutes. (Together, the on and off periods define a duty cycle.) For example, the control unit may drive the electrodes to apply the current having on periods of between about 60 seconds and about 105 seconds, and off periods of between about 30 seconds and 90 seconds, e.g., on periods of about 90 seconds, and off periods of about 60 seconds.

For some applications, the receiver comprises an electrical contact site, and the control unit is adapted to be coupled to the receiver by being brought into physical contact with the electrical contact site. For example, the control unit may be brought into physical contact by positioning the control unit inside an oral cavity of the subject. For some applications, the stimulation system comprises an oral appliance, adapted to be fixed to the control unit, and shaped so as to define a surface that fits closely to a roof of an oral cavity. For example, the oral appliance may be similar to oral appliance 518, described hereinabove with reference to FIG. 18.

Alternatively, the receiver comprises a transducer, and the control unit comprises a wireless transmitter, which is adapted to couple the control unit to the receiver via wireless electromagnetic communication with the transducer. Typically, the transducer comprises a coil. For some applications, the control unit is adapted to be positioned outside of a head of the subject. Alternatively, the control unit is adapted to be placed in the oral cavity, such as by being fixed to an oral appliance. For some applications, the receiver has a volume of less than about 0.8 cm$^3$, such as less than about 0.15 cm$^3$.

For some applications, stimulator 30 is implanted using techniques described in a US patent application filed May 11, 2005, entitled, "Surgical tools and techniques for stimulation," which is assigned to the assignee of the present application and is incorporated herein by reference.

In the present patent application, "SPG system" means the SPG and associated neuroanatomical structures, including neural tracts originating in or reaching the SPG, including outgoing and incoming parasympathetic and sympathetic tracts, which tracts include preganglionic fibers of the SPG (e.g., fibers contained within the vidian nerve) and postganglionic fibers of the SPG (fibers that travel anterogradely from the SPG toward the brain vascular bed, including the retro-orbital branches of the SPG, which are fibers that connect the SPG with orbital neural structures).

In an embodiment of the present invention, during placement of electrodes 38 at an MTS, as defined hereinabove, at least one physiological indicator of cerebral blood flow (CBF) is observed or measured concurrently with or after placement. For some applications, optimization of placement of electrodes 38 onto the appropriate neural structure is performed by activating the stimulator, and generally simultaneously monitoring CBF while manipulating the electrodes, and/or adjusting at least one parameter of the applied stimulation, so as to increase or decrease CBF, as appropriate. Alternatively or additionally, this technique is used to verify the placement of electrodes 38 after implantation, and/or to select which combination of electrodes to use, such as by using the feedback algorithm described hereinabove. Alternatively or additionally, a similar optimization process is performed, either during or after placement of electrodes 38, to determine parameters of the applied current so as to achieve a desired effect, e.g., on CBF or BBB permeability, as indicated by CBF.

Physiological indicators of CBF include, but are not limited to, the following:
- a measure of vasodilation of blood vessels of the eye, determined by unaided visual inspection or by using an instrument, e.g., an instrument comprising machine vision functionality;
- transcranial Doppler ultrasonography measurements;
- a measure of forehead perfusion, measured, for example, using laser Doppler perfusion imaging (LDI) and/or using a temperature sensor; and/or
- near infrared spectroscopy (NIRS) measurements.

Other appropriate measurements indicative of CBF for use with these embodiments of the present invention will be apparent to those skilled in the art, having read the disclosure of the present patent application.

For some applications, one or more of the devices described hereinbelow with reference to FIGS. 18-21 are used for assessing a physiological indicator of CBF.

FIG. 19 is a schematic illustration of a vasodilation measurement instrument 230, in accordance with an embodiment of the present invention. Instrument 230 comprises an image sensor 234 (e.g., a CCD or CMOS sensor, or another camera) and processing circuitry 238, in order to provide machine vision functionality. Image sensor 234 is directed towards an eye 232 of the subject. The instrument measures the ratio of red to white in the sclera of eye 232, or another indication of vasodilation.

FIG. 20 is a schematic illustration of a laser Doppler perfusion (LDI) device 270, in accordance with an embodiment of the present invention. LDI device 270 comprises a laser source 271, a scanner 272, and a computer 281. Scanner 272 is positioned near a forehead 241 of the subject for measuring forehead perfusion.

FIG. 21 is a schematic illustration of a thermometer 280, in accordance with an embodiment of the present invention. Thermometer 280 is positioned touching a forehead 241 of the subject for measuring forehead perfusion.

FIG. 22 is a schematic illustration of a transcranial Doppler ultrasonography device 284, in accordance with an embodiment of the present invention. Transcranial Doppler ultrasonography device 284 is positioned touching a head 288 of the subject for measuring CBF.

For some applications, the measurement device, such as those described hereinabove with reference to FIGS. 18-21, comprises an output unit 236, such as a numeric display, tone generator, color display, or other output device, for outputting a signal indicative of the measured physiological parameter. Alternatively or additionally, instrument 230 is coupled to an internal or external control unit of system 20 or 120, and communicates the signal directly to the control unit.

In an embodiment of the present invention, during placement of electrodes 38 at an MTS, as defined hereinabove, penetration of a systemically administered dye into an eye of the subject is observed or measured concurrently with or after placement, as an indication of a level of increased permeability of the BBB. For example, the dye may include fluorescein dye. For some applications, optimization of placement of electrodes 38 onto the appropriate neural structure is performed by activating the stimulator, and generally simultaneously monitoring the penetration of the dye while manipulating the electrodes, and/or adjusting at least one parameter of the applied stimulation, so as to increase or decrease permeability of the BBB, as appropriate. Alternatively or additionally, this technique is used to verify the placement of electrodes 38 after implantation, and/or to select which combination of electrodes to use, such as by using the feedback algorithm described hereinabove. Alternatively or additionally, a similar optimization process is performed, either during or after placement of electrodes 38, to determine parameters of the applied current so as to achieve a desired effect, e.g., on CBF or BBB permeability, as indicated by BBB permeability.

In an embodiment of the present invention, one or more of the above-described CBF-based assessment techniques are used by a healthcare worker after implantation to assess (a) whether electrodes 38 retain appropriate placement and contact with the MTS, and/or (b) whether parameters of the applied current (e.g., magnitude, frequency, duration, scheduling) continue to achieve the desired effect, e.g., on CBF or BBB permeability. For example, such an assessment may be performed periodically during post-implantation follow-up care.

In an embodiment of the present invention, the CBF-based assessment techniques described hereinabove are used to assist in determining the effective dosage and/or other parameters for presenting odorants to an air passage of the patient, as described in U.S. patent application Ser. No. 10/512,780, filed Oct. 25, 2004, which is assigned to the assignee of the present application and is incorporated herein by reference.

In an embodiment of the present invention, chemical stimulation of at least one MTS is achieved by presenting chemicals, for example in a liquid or gaseous state, to an air passage of the subject, such as a nasal cavity or a throat, or in a vicinity thereof. The temporal profile and other quantitative characteristics of such chemical modulation are believed by the present inventors to have a mechanism of action that has a neuroanatomical basis overlapping with that of the electrical modulation of the MTS. For some applications, chemical-presentation techniques described herein are practiced in combination with techniques described in U.S. patent application Ser. No. 10/512,780, filed Oct. 25, 2004, and/or U.S. patent application Ser. No. 10/952,536, filed Sep. 27, 2005, both of which are assigned to the assignee of the present patent application and are incorporated herein by reference. In these chemical-presentation applications, an extent to which the chemical has achieved the desired effect (e.g., increased permeability of the BBB, or increased or decreased CBF) is determined by monitoring real-time changes in CBF, and adjusting the dose of the chemical responsive thereto.

Chemicals that may increase or decrease cerebral blood flow and/or the permeability of the blood-brain barrier (e.g., via modulation of SPG-related fibers), include, but are not limited to, propionic acid, cyclohexanone, amyl acetate, acetic acid, citric acid, carbon dioxide, sodium chloride, ammonia, menthol, alcohol, nicotine, piperine, gingerol, zingerone, allyl isothiocyanate, cinnamaldehyde, cuminaldehyde, 2-propenyl/2-phenylethyl isothiocyanate, thymol, and eucalyptol. The chemicals reach the appropriate neural structures and induce vasodilatation, vasoconstriction and/or cerebrovascular permeability changes.

In an embodiments of the present invention, chemical stimulation is applied to at least one MTS, using (a) a nasal applicator adapted to deliver the stimulating chemical to an upper region of the nasal cavity, or (b) a transpalatine applicator inserted via the greater palatine canal.

In some embodiments of the present invention, stimulation of at least one MTS is achieved by applying a neuroexcitatory agent to the MTS. Suitable neuroexcitatory agents include, but are not limited to, acetylcholine and urocholine. For some applications, the MTS is stimulated by applying a neuroinhibitory agent, such as atropine, hexamethonium, or a local anesthetic (e.g., lidocaine). In these agent-application embodiments, an extent to which the agent has achieved the desired effect (e.g., increased permeability of the BBB, or increased or decreased CBF) is determined by monitoring real-time changes in CBF, and adjusting the dose of the agent responsive thereto.

In an embodiment of the present invention, stimulation of the MTS is achieved by applying mechanical stimulation to the MTS, e.g., vibration. An extent to which the mechanical stimulation has achieved the desired effect (e.g., increased permeability of the BBB, or increased or decreased CBF) is determined by monitoring real-time changes in CBF, and adjusting the extent of the mechanical stimulation (e.g., magnitude, frequency, or duration) responsive thereto.

It is also to be appreciated that whereas some embodiments of the present invention are described with respect to implanting the electrical stimulator, for some applications the stimulator is temporarily inserted into the subject, and techniques described herein are used to optimize the temporary placement of the stimulator.

In an embodiment of the present invention, bilateral stimulation is applied, in which a first electrode is applied to a first MTS, and a second electrode is applied to a second MTS. Such bilateral stimulation may be applied using techniques described in U.S. Provisional Patent Application 60/604,037, filed Aug. 23, 2004, which is assigned to the assignee of the present application and is incorporated herein by reference, and/or in PCT Patent Application PCT/IL2005/000912, filed Aug. 23, 2005," entitled, "Concurrent bilateral SPG modulation," which is assigned to the assignee of the present application and is incorporated herein by reference.

In some embodiments of the present invention, techniques described herein are practiced in combination with techniques described in one or more of the references cited in the Background of the Invention section hereinabove and/or in combination with techniques described in one or more of the patent applications cited hereinabove.

The scope of the present invention includes embodiments described in the following patent applications, which are assigned to the assignee of the present patent application and are incorporated herein by reference. In an embodiment of the present invention, techniques and apparatus described in one or more of the following applications are combined with techniques and apparatus described herein:

U.S. Provisional Patent Application 60/203,172, filed May 8, 2000, entitled, "Method and apparatus for stimulating the sphenopalatine ganglion to modify properties of the BBB and cerebral blood flow"

U.S. patent application Ser. No. 10/258,714, filed Oct. 25, 2002, entitled, "Method and apparatus for stimulating the sphenopalatine ganglion to modify properties of the BBB and cerebral blood flow," or the above-referenced PCT Publication WO 01/85094

U.S. Provisional Patent Application 60/364,451, filed Mar. 15, 2002, entitled, "Applications of stimulating the sphenopalatine ganglion (SPG)"

U.S. Provisional Patent Application 60/368,657, filed Mar. 28, 2002, entitled, "SPG Stimulation"

U.S. Provisional Patent Application 60/376,048, filed Apr. 25, 2002, entitled, "Methods and apparatus for modifying properties of the BBB and cerebral circulation by using the neuroexcitatory and/or neuroinhibitory effects of odorants on nerves in the head"

U.S. Provisional Patent Application 60/388,931, filed Jun. 14, 2002, entitled "Methods and systems for management of Alzheimer's disease," PCT Patent Application PCT/IL03/000508, filed Jun. 13, 2003, claiming priority therefrom, and U.S. patent application Ser. No. 10/518, 322, filed Dec. 14, 2004 in the national stage thereof U.S. Provisional Patent Application 60/400,167, filed Jul. 31, 2002, entitled, "Delivering compounds to the brain by modifying properties of the BBB and cerebral circulation"

U.S. Provisional Patent Application 60/426,180, filed Nov. 14, 2002, entitled, "Surgical tools and techniques for sphenopalatine ganglion stimulation," PCT Patent Application PCT/IL03/000966, filed Nov. 13, 2003, which claims priority therefrom, and U.S. patent application Ser. No. 10/535,024, filed May 11, 2005, in the national stage thereof U.S. Provisional Patent Application 60/426,182, filed Nov. 14, 2002, and corresponding PCT Patent Application PCT/IL03/000967, which claims priority therefrom, filed Nov. 13, 2003, entitled, "Stimulation circuitry and control of electronic medical device," and a US patent application filed May 11, 2005 in the national stage thereof U.S. patent application Ser. No. 10/294,310, filed Nov. 14, 2002, entitled, "SPG stimulation for treating eye pathologies," and PCT Patent Application PCT/IL03/000965, filed Nov. 13, 2003, claiming priority therefrom PCT Patent Application PCT/IL03/000631, filed Jul. 31, 2003, entitled, "Delivering compounds to the brain by modifying properties of the BBB and cerebral circulation," and a US patent application filed Jan. 31, 2005 in the national stage thereof U.S. Pat. No. 6,853,858 to Shalev U.S. patent application Ser. No. 10/783,113, filed Feb. 20, 2004, entitled, "Stimulation for acute conditions"

U.S. Provisional Patent Application 60/426,181, filed Nov. 14, 2002, entitled, "Stimulation for treating ear pathologies," PCT Patent Application PCT/IL03/000963, filed Nov. 13, 2003, which claims priority therefrom, and a US patent application filed May 11, 2005 in the national stage thereof U.S. Provisional Patent Application 60/448,807, filed Feb. 20, 2003, entitled, "Stimulation for treating autoimmune-related disorders of the CNS"

U.S. Provisional Patent Application 60/461,232 to Gross et al., filed Apr. 8, 2003, entitled, "Treating abnormal conditions of the mind and body by modifying properties of the blood-brain barrier and cephalic blood flow"

PCT Patent Application PCT/IL03/00338 to Shalev, filed Apr. 25, 2003, entitled, "Methods and apparatus for modifying properties of the BBB and cerebral circulation by using the neuroexcitatory and/or neuroinhibitory effects of odorants on nerves in the head," and U.S. patent application Ser. No. 10/512,780, filed Oct. 25, 2004 in the national stage thereof U.S. Provisional Patent Application 60/506,165, filed Sep. 26, 2003, entitled, "Diagnostic applications of stimulation"

U.S. patent application Ser. No. 10/678,730, filed Oct. 2, 2003, entitled, "Targeted release of nitric oxide in the brain circulation for opening the BBB," and PCT Patent Application PCT/IL04/000911, filed Oct. 3, 2004, claiming priority therefrom PCT Patent Application PCT/IL04/000897, filed Sep. 26, 2004, entitled, "Stimulation for treating and diagnosing conditions"

U.S. Provisional Patent Application 60/604,037, filed Aug. 23, 2004, entitled, "Concurrent bilateral SPG modulation"

PCT Patent Application PCT/IL2005/000912, filed Aug. 23, 2005, entitled, "Concurrent bilateral SPG modulation"

U.S. patent application Ser. No. 10/952,536, filed Sep. 27, 2004, entitled, "Stimulation for treating and diagnosing conditions"

U.S. Provisional Patent Application 60/709,734, filed Aug. 19, 2005, entitled, "Stimulation for treating brain events and other conditions"

In an embodiment of the present invention, system 20 and/or 120 comprises circuitry described in one or more of the above-mentioned applications.

As used in the present application, the BBB comprises the tight junctions opposing the passage of most ions and large molecular weight compounds between the blood and brain tissue.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. For example, elements which are shown in a figure to be housed within one integral unit may, for some applications, be disposed in a plurality of distinct units. Similarly, apparatus for communication and power transmission which are shown to be coupled in a wireless fashion may, alternatively, be coupled in a wired fashion, and apparatus for communication and power transmission which are shown to be coupled in a wired fashion may, alternatively, be coupled in a wireless fashion.

The invention claimed is:

1. Apparatus for modifying a property of a brain of a subject, comprising:

at least one electrode, configured to be positioned in a vicinity of a mucous membrane of a palate of an oral cavity of the subject;

a control unit, configured to drive the electrode to apply a transmucosal electrical current to the mucous membrane, and to configure the current to be capable of inducing an increase in cerebral blood flow (CBF) of the subject; and an oral appliance, which comprises the at least one electrode, and which is configured to bring the at least one electrode into contact with the mucous membrane for applying the transmucosal electrical current.

2. The apparatus according to claim 1, wherein the control unit is configured to configure the current to have a magnitude sufficient to activate a sphenopalatine ganglion (SPG) of the subject via nerve fibers in physical contact with the mucous membrane.

3. The apparatus according to claim 1, wherein the control unit is configured to configure the current to increase the CBF to a magnitude sufficient to treat a condition of the subject.

4. The apparatus according to claim 1, wherein the oral appliance is shaped generally similarly to an orthodontic retainer.

5. The apparatus according to claim 1, wherein the oral appliance is shaped so as to define a surface that fits closely to a roof of the oral cavity.

6. A method for modifying a property of a brain of a subject, comprising:

transmucosally applying an electrical current to nerve fibers within or immediately above a mucous membrane of a palate of an oral cavity of the subject; and configuring the current to induce an increase in cerebral blood flow (CBF) of the subject.

7. The method according to claim 6, comprising administering a sedative to the subject in conjunction with applying the current.

8. The method according to claim 6, comprising administering an anesthetic to the subject in conjunction with applying the current.

9. The method according to claim 6, wherein applying the current comprises configuring the current to have a magnitude sufficient to activate a sphenopalatine ganglion (SPG) of the subject via nerve fibers in physical contact with the mucous membrane.

10. The method according to claim 6, wherein applying the current comprises configuring the current to increase the CBF to a magnitude sufficient to treat a condition of the subject.

11. The method according to claim 6, wherein applying the current comprises bringing an oral appliance into contact with the mucous membrane, and applying the current from the oral appliance.

12. A method for modifying a property of a brain of a subject, comprising:

applying an electrical current to a mucous membrane of a palate of an oral cavity of the subject, using one or more electrodes in contact with the mucous membrane; and configuring the current to induce an increase in cerebral blood flow (CBF) of the subject.

13. The method according to claim 12, wherein applying the current comprises configuring the current to have a magnitude sufficient to activate a sphenopalatine ganglion (SPG) of the subject via nerve fibers in physical contact with the mucous membrane.

* * * * *